(12) United States Patent  
Barlogie et al.

(10) Patent No.: US 9,822,419 B2  
(45) Date of Patent: Nov. 21, 2017

(54) GEP5 MODEL FOR MULTIPLE MYELOMA

(71) Applicant: BioVentures, LLC, Little Rock, AR (US)

(72) Inventors: Bart Barlogie, Little Rock, AR (US); Pingping Qu, Little Rock, AR (US); Christoph Heuck, Little Rock, AR (US); Joshua Epstein, Little Rock, AR (US)

(73) Assignee: BioVentures, LLC, Little Rock, AR (US)

( * ) Notice: Subject to any disclaimer, the term of this patent is extended or adjusted under 35 U.S.C. 154(b) by 0 days.

(21) Appl. No.: 14/892,555

(22) PCT Filed: May 19, 2014

(86) PCT No.: PCT/US2014/038626  
§ 371 (c)(1),  
(2) Date: Nov. 19, 2015

(87) PCT Pub. No.: WO2014/189843  
PCT Pub. Date: Nov. 27, 2014

(65) Prior Publication Data  
US 2016/0102362 A1    Apr. 14, 2016

Related U.S. Application Data

(60) Provisional application No. 61/825,396, filed on May 20, 2013.

(51) Int. Cl.  
*C12Q 1/68* (2006.01)  
*G06F 19/20* (2011.01)

(52) U.S. Cl.  
CPC .......... *C12Q 1/6886* (2013.01); *G06F 19/20* (2013.01); *C12Q 2600/118* (2013.01); *C12Q 2600/158* (2013.01); *C12Q 2600/16* (2013.01)

(58) Field of Classification Search  
None  
See application file for complete search history.

(56) References Cited

U.S. PATENT DOCUMENTS

| | | |
|---|---|---|
| 7,308,364 B2 | 12/2007 | Shaughnessy et al. |
| 7,711,492 B2 | 5/2010 | Staudt et al. |
| 7,741,035 B2 | 6/2010 | Shaughnessy et al. |
| 7,863,424 B2 | 1/2011 | Dalla-Favera |
| 7,935,679 B2 | 5/2011 | Shaughnessy et al. |
| 8,843,320 B2 | 9/2014 | Shaughnessy et al. |
| 2003/0036163 A1 | 2/2003 | Wettstein et al. |
| 2003/0165831 A1 | 9/2003 | Lee et al. |
| 2004/0009523 A1 | 1/2004 | Shaughnessy et al. |
| 2004/0009541 A1 | 1/2004 | Singh et al. |
| 2005/0164231 A1 | 7/2005 | Staudt et al. |
| 2005/0260664 A1 | 11/2005 | Shaughnessy et al. |
| 2010/0316629 A1* | 12/2010 | Shaughnessy, Jr. .  C12Q 1/6886 424/130.1 |
| 2013/0338025 A1 | 12/2013 | Shaughnessy et al. |
| 2014/0179545 A1 | 6/2014 | Shaughnessy et al. |

FOREIGN PATENT DOCUMENTS

| | | |
|---|---|---|
| EP | 2 390 662 A1 | 11/2011 |
| WO | WO-03/038088 A1 | 5/2003 |
| WO | WO-2004/031412 A2 | 4/2004 |
| WO | WO-2004/053066 A2 | 6/2004 |
| WO | WO-2005/024043 A2 | 3/2005 |
| WO | WO-2005/116259 A2 | 12/2005 |
| WO | WO-2006/133361 A2 | 12/2006 |
| WO | WO-2011/153545 A2 | 12/2011 |
| WO | WO-2013/071247 A1 | 5/2013 |

OTHER PUBLICATIONS

Hudelist et al. (Proteomics, 6:1989-2002, 2006).*
Edmondson, R.D. et al. (2012) "Combining Proteomics and Gene Expression Profiling Identifies Proteins/Genes Associated with Short Overall Survival in Multiple Myeloma," Blood 120(21):197; 54th Annual Meeting and Exposition of the American Society of Hematology (ASH); Atlanta, GA, USA; Dec. 8-11, 2012.
Upparahallivenkateshaiah, S. et al. (2012) "Upregulation of Lipid Metabolism Modulators in Myeloma Cells Underlines Their Progression in a Supportive Microenvironment and Linking Metabolic Pathways with Growth Signaling," Blood 120(21):329; 54th Annual Meeting and Exposition of the American Society of Hematology (ASH); Atlanta, GA, USA; Dec. 8-11, 2012.
International Search Report (ISA/EP)for International Application No. PCT/US2014/038626, dated Sep. 22, 2014, 5 pages.
Advisory Action in U.S. Appl. No. 11/133,937, dated Jan. 25, 2011.
Advisory Action in U.S. Appl. No. 11/133,937, dated Sep. 18, 2013.
Advisory Action in U.S. Appl. No. 11/147,829, dated Jul. 24, 2009.
Advisory Action in U.S. Appl. No. 12/799,874, dated Feb. 11, 2014.
Advisory Action in U.S. Appl. No. 12/799,874, dated May 20, 2015.
Avet-Loiseau, H. et al. (1997) "Molecular cytogenetic abnormalities in multiple myeloma and plasma cell leukemia measured using comparative genomic hybridization," Genes, Chromosomes and Cancer 19(2):124-133.
Barlogie, B. et al. (2004) "Treatment of multiple myeloma," Blood 103(1):20-32.
Cole, K.A. et al. (1999) "The genetics of cancer—a 3D model," Nature Genetics Supplement 21:38-41.
Dhondapkar, M.V. et al. (2013) "Clinical, genomic, and imaging predictors of malignancy: Analysis of the first U.S. cooperative group prospective clinical trial in asymptomatic monoclonal gammopathies (SWOG S0120)," J. Clin. Oncol. 31(Suppl.):Abstract 8515.

(Continued)

*Primary Examiner* — Brad Duffy  
*Assistant Examiner* — Nelson B Moseley, II  
(74) *Attorney, Agent, or Firm* — Foley & Lardner LLP

(57) ABSTRACT

The invention provides, inter alia, methods of prognosing a subject with, or suspected of having, multiple myeloma. In certain embodiments, the methods entail testing the gene expression levels of enolase 1 (ENO1), fatty acid binding protein 5 (FABP5), thyroid hormone receptor interactor 13 (TRIP 13), transgelin 2 (TAGLN2), and replication factor C (activator 1) 4 (RFC4) in a biological sample isolated from the subject. The invention also provides methods of treatment for multiple myeloma, as well as kits, oligonucleotides, and systems for performing the methods provided by the invention.

31 Claims, 13 Drawing Sheets

(56) References Cited

OTHER PUBLICATIONS

Final Office Action in U.S. Appl. No. 11/133,937, dated Apr. 13, 2009.
Final Office Action in U.S. Appl. No. 11/133,937, dated Aug. 19, 2010.
Final Office Action in U.S. Appl. No. 11/133,937, dated Jun. 12, 2013.
Final Office Action in U.S. Appl. No. 11/147,829, dated Mar. 31, 2009.
Final Office Action in U.S. Appl. No. 11/983,113, dated Feb. 5, 2015.
Final Office Action in U.S. Appl. No. 12/799,874, dated Aug. 6, 2013.
Final Office Action in U.S. Appl. No. 12/799,874, dated Dec. 10, 2014.
Final Office Action in U.S. Appl. No. 12/799,874, dated Feb. 27, 2013.
Final Office Action in U.S. Appl. No. 13/899,196, dated Oct. 12, 2016.
Kitajima, S. et al. (2004) "Role of Cks1 overexpression in oral squamous cell carcinomas—Cooperation with Skp2 in promoting p27 degradation," American Journal of Pathology 165(6):2147-2155.
Lockhart, D.J. et al. (2000) "Genomics, gene expression and DNA arrays," Nature 405:827-836.
Mangrangeas, F. et al. (2003) "Gene expression profiling of multiple myeloma reveals molecular portraits in relation to the pathogenesis of the disease," Blood 101(12):4998-5006.
Non-Final Office Action in U.S. Appl. No. 11/133,937, dated Dec. 17, 2013.
Non-Final Office Action in U.S. Appl. No. 11/133,937, dated Dec. 28, 2009.
Non-Final Office Action in U.S. Appl. No. 11/133,937, dated Sep. 4, 2008.
Non-Final Office Action in U.S. Appl. No. 11/147,829, dated Sep. 5, 2008.
Non-Final Office Action in U.S. Appl. No. 12/799,874, dated Oct. 3, 2012.
Non-Final Office Action in U.S. Appl. No. 12/799,874, dated Sep. 21, 2015.
Non-Final Office Action in U.S. Appl. No. 13/899,196, dated Jan. 4, 2016.
Notice of Allowance in U.S. Appl. No. 11/133,937, dated May 21, 2014.
Notice of Allowance in U.S. Appl. No. 11/147,829, dated Jan. 22, 2010.
Notice of Allowance in U.S. Appl. No. 13/899,196, dated Jan. 10, 2017.
Restriction Requirement in U.S. Appl. No. 11/133,937, dated Mar. 18, 2008.
Restriction Requirement in U.S. Appl. No. 11/147,829, dated Mar. 25, 2008.
Restriction Requirement in U.S. Appl. No. 12/799,874, dated Aug. 14, 2012.
Sawyer, J.R. et al. (2004) "Genomic instability in multiple myeloma: Evidence for jumping segmental duplications of chromosome arm 1q," Genes, Chromosomes and Cancer 42(1):95-106.
Shaughnessy, J. (2005) "Amplification and overexpression of CKS1B at chromosome band 1q21 is associated with reduced levels of p27(Kip1) and an aggressive clinical course in multiple myeloma," Hematology 10(Suppl. 1):117-126.
Shaughnessy, J.D., Jr. et al. (2006) "A Validated Gene Expression Model of High-Risk Multiple Myeloma is Defined by Deregulated Expression of Genes Mapping to Chromosome 1," Blood, doi: 10.1182/blood-2006-07-038430.
Tsai, Y-S. et al. (2005) "RNA Silencing of Cks1 Inducing G2/M Arrest and Apoptosis in Human Lung Cancer Cells," IUBMB Life 57(8):583-589.
Woerner, S.M. et al. (2007) "The Putative Tumor Suppressor AIM2 is Frequently Affected by Different Genetic Alterations in Microsatellite Unstable Colon Cancers," Genes, Chromosomes & Cancer 46:1080-1089.
Zhan, F. et al. (2002) "Global Gene Expression Profiling of Multiple Myeloma, Monoclonal Gammopathy of Undermined Significance, and Normal Bone Marrow Plasma Cells," American Society of Hematology 99(5):1745-1757.
Zhan, F. et al. (2003) "Gene expression profiling of human plasma cell differentiation and classification of multiple myeloma based on similarities to distinct stages of late-stage B-cell development," Blood 101(3):1128-1140.
Zhan, F. et al. (2004) "Elevated Expression of CKS1B at 1q21 Is Highly Correlated with Short Survival in Myeloma," Blood 104(11):77.
Zhan, F. et al. (2005) "DNA amplification and over-expression of CKS1B is inversely correlated with p27 levels and associated with aggressive clinical course in multiple myeloma (MM)," Proceedings of the Annual Meeting of the American Association for Cancer Research 46:638.

\* cited by examiner

GEP5 MODEL FOR MULTIPLE MYELOMA

CROSS-REFERENCE TO RELATED APPLICATIONS

This application is a national stage entry under 35 U.S.C. §371 of International Application No. PCT/US2014/038626, filed May 19, 2014, which in turn claims the benefit of U.S. Provisional Application No. 61/825,396, filed May 20, 2013, the content of each of which is incorporated herein by reference in its entirety.

The entire teachings of the above application are incorporated herein by reference.

GOVERNMENT SUPPORT

This invention was made with government support under P01CA055819 awarded by the National Institutes of Health. The government has certain rights in the invention.

BACKGROUND OF THE INVENTION

Multiple myeloma is the second most common hematological malignancy in the U.S., constituting about 1% of all diagnosed cancers. Multiple myeloma develops in about 1-4 per 100,000 people per year. Survival times amongst patients are varied—with conventional treatment, median survival is 3-4 years, which may be extended, in some patients, to 5-7 years or longer with advanced treatments. Patients are not uniform in their need for certain advanced therapies, however, so there are additional burdens on all affected parties when advanced treatments are improperly applied or withheld.

Given the immense personal and financial burden of multiple myeloma on patients, their social networks, and the healthcare system, and the varied survival times and responses to treatments, a need exists for methods for the prognosis of subjects that have, or are suspected of having, multiple myeloma. Preferably, such methods should be capable of stratifying subjects based on genetic information, particularly when limited amounts of genetic material are available for the prognosis.

SUMMARY OF THE INVENTION

The invention provides methods of prognosing subjects that have, or are suspected of having, multiple myeloma. Advantageously, the methods provided by the invention are capable of prognosing subjects using a limited amount of genetic material. The invention is based, at least in part, on Applicant's discovery of a small set of (five, or even as few as two) informative genes whose expression levels can be used to stratify subjects with multiple myeloma—in some embodiments using a biological sample with a limited number of cells.

In a first aspect, the invention provides methods of prognosing a subject suspected of having multiple myeloma. The methods include the steps of: testing the gene expression level of enolase 1 (ENO1), fatty acid binding protein 5 (FABP5), thyroid hormone receptor interactor 13 (TRIP13), transgelin 2 (TAGLN2), and replication factor C (activator 1) 4 (RFC4) in a biological sample isolated from the subject using a method capable of detecting the expression level of the genes when the biological sample comprises about 50,000 or fewer myeloma cells; and quantifying the gene expression levels of each of ENO1, FABP5, TRIP13, TAGLN2, and RFC4, where an abnormal gene expression profile as compared to a suitable control is associated with a poor prognosis for the subject. In some embodiments, the poor prognosis is reduced likelihood of overall survival (OS) and/or reduced likelihood of progression-free survival (PFS).

In certain embodiments, the methods provided by the invention include a step of assigning the subject a prognosis on the basis of the tested gene expression levels, e.g., on the basis of a presence or absence of an abnormal gene expression profile.

In some embodiments, the gene expression levels are tested at the protein level.

In other embodiments, the gene expression levels are tested at the nucleic acid level. In more particular embodiments, the gene expression levels are tested by quantitative polymerase chain reaction (qPCR), quantitative real-time polymerase chain reaction (qRTPCR), digital droplet PCR, (ddPCR), sequencing, northern blotting, or Southern blotting. In more particular embodiments, the gene expression levels are tested by qRTPCR. In still more particular embodiments, the gene expression levels are tested by qRTPCR comprising the use of sets of three primers for each of the genes, wherein for each set of three primers at least one of the primers is detectably labeled and is subject to polymerase-dependent hydrolysis in the presence of the target template of the set of three primers—e.g., TAQMAN®. In still more particular embodiments, the detectable label is a fluorescent label. In other particular embodiments, the gene expression levels are tested by qRTPCR using primers selected from Hs00361415_m1, Hs02339439_g1, Hs00188500_m1, Hs00761239_s1, Hs00427469_m1, primers listed in Table B, or primers substantially similar to those listed in Table B.

In some embodiments, the subject is undergoing myeloma therapy.

In particular embodiments, the method is capable of prognosing OS in a subject undergoing TT2.

In other particular embodiments, the method is capable of prognosing both OS and PFS in a subject undergoing TT3a.

In some embodiments, the method is capable of prognosing PFS in a subject undergoing TT3b.

In other embodiments, the method is capable of prognosing PFS in a subject undergoing TT4 or TT5. In more particular embodiments, the method is capable of prognosing both OS and PFS in a subject undergoing TT4 or TT5.

In some embodiments, the method is capable of prognosing OS in a subject undergoing TT6.

In another aspect, the invention provides method of prognosing progression free survival (PFS) in a subject with multiple myeloma undergoing Total Therapy 3b (TT3b). These methods include the steps of: testing the gene expression level of enolase 1 (ENO1), fatty acid binding protein 5 (FABP5), thyroid hormone receptor interactor 13 (TRIP13), transgelin 2 (TAGLN2), and replication factor C (activator 1) 4 (RFC4) in a biological sample isolated from the subject; and quantifying the gene expression levels of each of ENO1, FABP5, TRIP13, TAGLN2, and RFC4, where an abnormal gene expression profile is associated with a reduced likelihood of PFS for the subject.

In another aspect, the invention provides methods of prognosing progression free survival (PFS) or overall survival (OS) in a subject with multiple myeloma undergoing Total Therapy 4 (TT4) or Total Therapy 5 (TT5) by testing the gene expression level of enolase 1 (ENO1), fatty acid binding protein 5 (FABP5), thyroid hormone receptor interactor 13 (TRIP13), transgelin 2 (TAGLN2), and replication factor C (activator 1) 4 (RFC4) in a biological sample isolated from the subject and quantifying the gene expression levels of each of ENO1, FABP5, TRIP13, TAGLN2, and RFC4, where an abnormal gene expression profile is associated with a reduced likelihood of PFS or OS for the subject. In particular embodiments, the method is for prognosing OS. In other particular embodiments, an abnormal gene expression profile is an independent averse factor for PFS as evaluated by stepwise regression.

In some embodiments of any of the preceding aspects and embodiments, the subject is a human.

In particular embodiments of any of the preceding aspects or embodiments, the subject exhibits an abnormal gene expression profile and is thereby determined to have a poor prognosis and is changed to more frequent surveillance schedule.

In particular embodiments of any of the preceding aspects or embodiments, the subject does not exhibit an abnormal gene expression profile and is thereby determined to have a favorable prognosis.

In particular embodiments of any of the preceding aspects or embodiments, the subject is undergoing treatment with a proteasome inhibitor, an immunomodulatory drug, cisplatin, etoposide, cyclophosphamide, melphalan, cellular therapy with expanded NK cells, cellular therapy with T-cells, antibody therapy, dexamethasone, or combinations thereof.

In particular embodiments of any of the preceding aspects or embodiments, the gene expression levels are log-normalized.

In some embodiments of any of the preceding aspects or embodiments, the disease index is calculated as the mean of log-normalized gene expression levels of the genes.

In particular embodiments of any of the preceding aspects or embodiments, the method discriminates between poor and favorable prognosis for OS or PFS with a hazard ratio of at least 1.5, 1.6, 1.7, 1.8, 1.9, 2.0, 2.2, 2.4, 2.6, 2.8, 3.0, 3.2, 3.4, 3.6, 3.8, 4.0, 4.2, 4.4, 4.6, 4.8, 5.0, 5.2, 5.4, 5.6, 5.8, or 6.0.

In some embodiments of any of the preceding aspects or embodiments, the biological sample comprises fewer than 45,000; 40,000; 30,000; 20,000; 10,000; 9,000; 8,000; 7,000; 6,000; 5,000; 4,000; 3,000; 2,000; 1,000; 900; 800; 700; 600; 500; 400; 300; 200; 100; 90; 80; 70; 60; 50; 40; 30; 20; 10; 9; 8; 7; 6; 5; 4; 3; or 2 myeloma cells. In particular embodiments, the myeloma cells are selected by $CD138^+$ expression, $CD38^+/CD45^{dim}$ expression, or $CD38^+/CD45^{neg}$ expression.

In another aspect, the invention provides methods of prognosing a subject suspected of having multiple myeloma by testing, by qRT-PCR, the nucleic acid gene expression level of enolase 1 (ENO1), fatty acid binding protein 5 (FABP5), thyroid hormone receptor interactor 13 (TRIP13), transgelin 2 (TAGLN2), and replication factor C (activator 1) 4 (RFC4) in a nucleic acid sample isolated from a biological sample isolated from the subject and calculating the mean, log-normalized gene expression level of ENO1, FABP5, TRIP13, TAGLN2, and RFC4, where an elevated mean, log-normalized gene expression level of ENO1, FABP5, TRIP13, TAGLN2, and RFC4, relative to a suitable control, is associated with a poor prognosis for the subject.

In yet another aspect, the invention provides methods of treating multiple myeloma in a subject, comprising administering a suitable therapy to the subject on the basis of a prognosis by the method of any one of the preceding aspects and embodiments.

In another aspect, the invention provides kits containing reagents for performing the method of any of the preceding aspects and embodiments, optionally including suitable positive and/or negative controls. In more particular embodiments, the kit includes one or more of any one of the primers Hs00361415_m1, Hs02339439_g1, Hs00188500_m1, Hs00761239_s1, Hs00427469_m1, those listed in Table B, or primers substantially similar to those listed in Table B.

In yet another aspect, the invention provides a non-transitory computer-readable storage medium that provides instructions that, if executed by a processor, causes the processor to perform operations including: reading data representing the gene expression level of enolase 1 (ENO1), fatty acid binding protein 5 (FABP5), thyroid hormone receptor interactor 13 (TRIP13), transgelin 2 (TAGLN2), and replication factor C (activator 1) 4 (RFC4) determined for an isolated biological sample obtained from a subject; analyzing the data to determine the presence of an abnormal gene expression profile as compared to a suitable control; and providing a classification of the subject on the basis of the data analysis, wherein the presence of an abnormal gene expression profile is associated with a poor prognosis for the subject. In some embodiments, the instructions further comprise a step of providing a therapeutic recommendation on the basis of the data analysis.

In another aspect, the invention provides a system comprising the storage medium of the preceding aspect and a processor.

In another aspect, the invention provides methods of any one of the preceding aspects and embodiments where the presence of an abnormal gene expression profile is determined using a storage medium or system provided by the invention.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 1A shows the TT6 training set results. GEP 5 identified a high-risk subset with a 1-year estimate OS of 60% (left panel) and PFS of 50% (right panel), compared to 95% and 91%, respectively, for GEP5 low-risk. FIG. 1B shows the TT3A training set results. GEP 5 identified a high-risk subset with a 5-year estimate OS of 38% (left panel) and PFS of 33% (right panel), compared to 81% and 71%, respectively, for GEP5 low-risk. FIG. 1C shows the TT3B validation set results. GEP 5 identified a high-risk subset with a 5-year estimate OS of 45% (left panel) and PFS of 31% (right panel), compared to 80% and 74%, respectively, for GEP5 low-risk. FIG. 1D shows the TT2 validation set results. GEP 5 identified a high-risk subset with a 5-year estimate OS of 40% (left panel) and PFS of 26% (right panel), compared to 71% and 49%, respectively, for GEP5 low-risk.

FIG. 2A shows the TT6 training set results. 2-year estimate for OS of 18% (left panel) and PFS of 19% (right panel) for GEP70 high-risk, compared to 95% and 72%, respectively, for GEP70 low-risk. FIG. 2B shows the TT3A training set results. 5-year estimate for OS of 35% (left panel) and PFS of 25% (right panel) for GEP70 high-risk, compared to 80% and 72%, respectively, for GEP7 low-risk. FIG. 3C shows the TT3B validation set results. 5-year estimate for OS of 38% (left panel) and PFS of 35% (right panel) for GEP70 high-risk, compared to 80% and 70%, respectively, for GEP70 low-risk. FIG. 3D shows the TT2 validation set results. 5-year estimate OS of 28% (left panel) and PFS of 15% (right panel) for GEP70 high-risk, compared to 72% and 50%, respectively, for GEP70 low-risk.

FIGS. 4A-4B are Kaplan-Meier plots comparing performances of the GEP5 and GEP70 model by treatment arm of TT2. FIG. 4A shows the TT2 thalidomide arm (thal+) results. GEP5 (upper panels; FIG. 4A-1) identified a high- and a low-risk group in the TT2+thal arm for OS (left panels) and PFS (right panels). GEP70 (lower panels; FIG. 4A-2), which was developed on TT2, showed a slightly better performance for OS and PFS. FIG. 4B shows the TT2 non-thalidomide arm (thal−) results. GEP5 (upper panels; FIG. 4B-1) could identify a high- and a low-risk group in the TT2−thal arm for OS (left panels) and PFS (right panels). GEP70 (lower panels; FIG. 4B-2), which was developed on TT2, showed a slightly better performance for OS and PFS.

DETAILED DESCRIPTION OF THE INVENTION

Figure 1A:
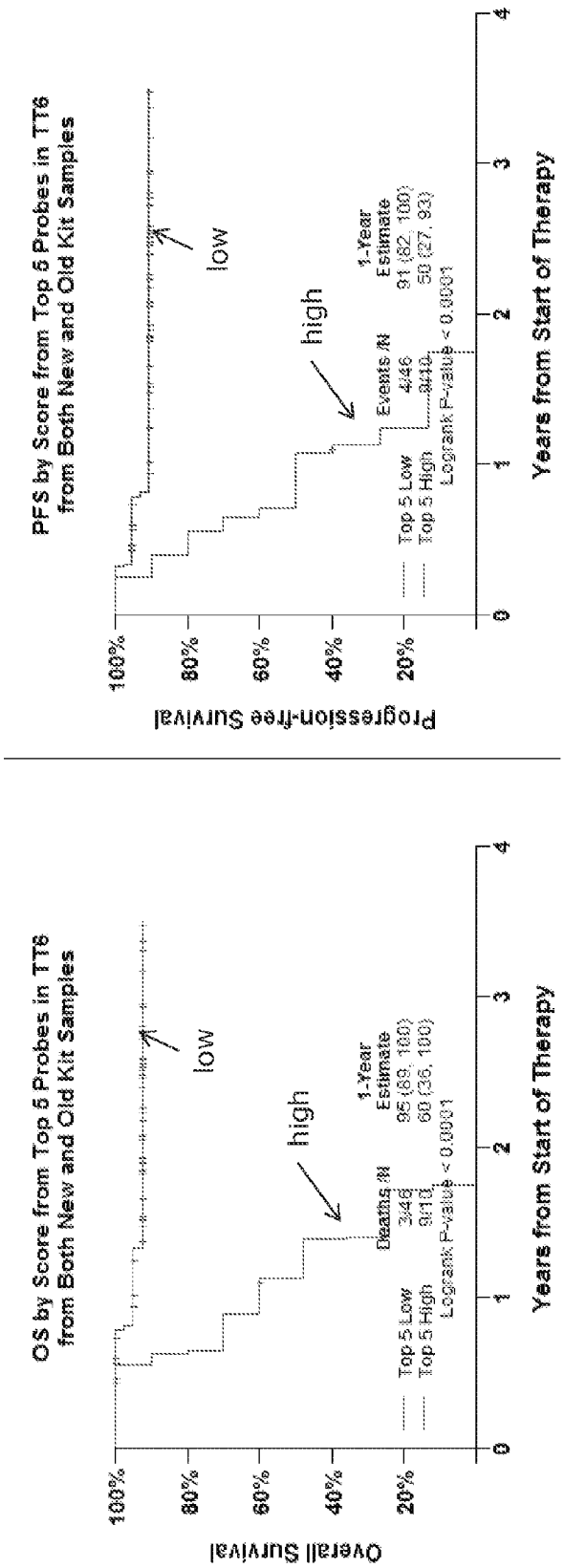
FIGS. 1A-1D are Kaplan-Meier plots illustrating that GEP5 distinguished a high- and a low-risk group with significantly different overall and progression free survival in the TT6 and TT3A training sets as well as the TT3B and TT2 validation sets.

A description of example embodiments of the invention follows.

Prognostic Methods

The invention provides, inter alia, prognostic methods—and kits and reagents for performing the methods—for subjects with, or suspected of having, multiple myeloma. The methods are based on gene expression profiling using (comprising, consisting essentially of, or consisting of) the genes listed in Table A, including, in some embodiments, any subset thereof, e.g., using 2 (e.g., ENO1 and FABP5), 3 (e.g., ENO1, FABP5, and TRIP13), 4 (e.g., ENO1, FABP5, TRIP13, and TAGLN2), or all 5 genes. In a preferred embodiment, all five of ENO1, FABP5, TRIP13, TAGLN2, and RFC4 are used. The genes listed in Table A are human reference sequences, and homologues from other mammalian species are known in the art and may be easily obtained from reference databases (such as the NCBI Entrez portal) using, inter alia, the information in Table A.

TABLE A

| Gene Symbol | GeneID | RefRNA | RefProtein |
| --- | --- | --- | --- |
| ENO1 | 2023 | NM_001201483.1 | NP_001188412.1 |
| | | NM_001428.3 | NP_001419.1 |
| FABP5 | 2171 | NM_001444.2 | NP_001435.1 |
| TRIP13 | 9319 | NM_001166260.1 | NP_001159732.1 |
| | | NM_004237.3 | NP_004228.1 |
| TAGLN2 | 8407 | NM_003564.1 | NP_003555.1 |
| RFC4 | 5984 | NM_002916.3 | NP_002907.1 |
| | | NM_181573.2 | NP_853551.1 |

In some embodiments, the gene expression profiling of genes comprising those in Table A, as well as subsets thereof, omits at least one (e.g., 1, 2, 3, 4, 5, 7, 8, 9, 10, 15, 20, 25, 30, 35, 40, 45, 50, 55, or all 56) of: GNG10, PNPLA4, KIAA1754, AHCYL1, MCLC, EVI5, AD-020, PARG1, CTBS, FUCA1, RFP2, FLJ20489, LTBP1, AIM2, SELI, SLC19A1, LARS2, OPN3, ASPM, CCT2, UBE21, STK6, FLJ13052, FLJ12525, BIRC5, CKS1B, CKAP1, MGC57827, DKFZp7790175, PFN1, ILF3, IF116, TBRG4, PAPD1, EIF2C2, MGC4308, DSG2, EXOSC4, RUVBL1, ALDOA, CPSF3, MGC15606, LGALS1, RAD18, SNX5, PSMD4, RAN, KIF14, CBX3, TMPO, DKFZP586L0724, WEE1, ROBO1, TCOF1, YWHAZ, and MPHOSPH1. In certain embodiments, the gene expression profiling of genes comprising those in Table A, as well as subsets thereof, omits at least one (e.g., 1, 2, 3, 4, 5, 7, 8, 9, 10, 15, 20, 25, 30, 35, 40, 45, 50, 55, 60, or all 65) of a gene detectable with one of the following AFFYMETRIX® AffyIDs: 1555864_s_at, 206513_at, 1555274_a_at, 211576_s_at, 204016_at, 1565951_s_at, 219918_s_at, 201947_s_at, 213535_s_at, 204092_s_at, 213607_x_at, 208117_s_at, 210334_x_at, 201897_s_at, 216194_s_at, 225834_at, 238952_x_at, 200634_at, 208931_s_at, 206332_s_at, 220789_s_at, 218947_s_at, 213310_at, 224523_s_at, 217901_at, 226936_at, 58696_at, 201614_s_at, 200966_x_at, 225082_at, 242488_at, 243011_at, 201105_at, 224200_s_at, 222417_s_at, 210460_s_at, 200750_s_at, 206364_at, 201091_s_at, 203432_at, 221970_s_at, 212533_at, 213194_at, 244686_at, 200638_s_at, 205235_s_at, 201921_at, 227278_at, 209740_s_at, 227547_at, 225582_at, 200850_s_at, 213628_at, 209717_at, 222495_at, 1557277_a_at, 1554736_at, 218924_s_at, 226954_at, 202838_at, 230192_at, 48106_at, 237964_at, 202729_s_at, and 212435_at.

"Prognosing" is assigning a risk stratification to a subject for one of at least two different risk groups for a clinical indicator. In particular embodiments, the at least two risk groups comprise poor prognosis and favorable prognosis for a clinical indicator. Exemplary clinical indicators include two year overall survival (OS) and two year progression free survival (PFS).

A "subject" is a mammal, including primates (e.g., humans or monkeys), cows, sheep, goats, horses, dogs, cats, rabbits, guinea pigs, rats, and mice, or other bovine, ovine, equine, canine, feline, rodent or murine species. Examples of suitable subjects include, but are not limited to, human patients (e.g., a human with, or suspected of having, multiple myeloma). The subject can be at any stage of development, including prenatal, perinatal, infant, toddler, child, young adult, adult, middle-aged, or geriatric. In more particular embodiments, the subject is a young adult, adult, middle-aged, or geriatric. In some embodiments, the subject is undergoing a myeloma treatment as defined below. In certain embodiments, a myeloma treatment may be indicated (or modified) based on the results of the methods provided by the invention. Where a subject prognosed by a method provided by the invention is "undergoing" any therapy, such as a myeloma therapy, such as TT1, TT2, TT3, TT4, TT5, or TT6, the biological sample can be obtained before, during, after, or a combination thereof (i.e., 1, 2, or all 3 of before, during, or after the treatment).

"Multiple myeloma" includes subjects with symptomatic myeloma, asymptomatic myeloma, and monoclonal gammopathy of undetermined significance (MGUS), as defined in Kyle and Rajkumar, *Leukemia* 23:3-9 (2009, PubMedID 18971951, incorporated by reference in its entirety), as well as the other stratifications and stages described in Kyle and Rajkumar 2009. In particular embodiments, "multiple myeloma" is symptomatic myeloma.

"Gene expression" refers to both nucleic acid level (e.g., mRNA or cDNA derived from it) and protein level expression of a gene. Genes expressed as nucleic acids may or may not encode for and/or be translated into protein. The physical product of gene expression is a "gene expression product."

"Level of expression," "expression level," "gene expression level" and the like are the amount of a gene expression product (e.g., nucleic acid or protein). Expression levels may be transformed (e.g., normalized) or analyzed "raw."

"Expression profile" or "gene expression profile" means at least two gene expression levels. For example, in some embodiments, the two or more gene expression levels may be the gene expression level of one gene at two or more time points or the expression levels of two or more different genes at the same, or different, times. For example, in particular embodiments, an expression profile is the expression level of ENO1, FABP5, TRIP13, TAGLN2, and RFC4 at one or more time points.

"Abnormal gene expression profile" refers to a significant statistical and/or practical deviation in the expression level of one or more genes, relative to a suitable control. "Suitable controls" include, for example, paired samples from a single patient (e.g., biological samples obtained at different times from a patient, e.g., before and after developing multiple myeloma) as well as reference values (such as an ensemble of reference values representing ranges associated with a particular prognosis) previously compiled from samples determined—by any means—to have a particular prognosis (e.g., poor or favorable prognosis). For example, reference values for one or more genes (e.g., all five of ENO1, FABP5, TRIP13, TAGLN2, and RFC4) may be compiled and used to develop a binary or probabilistic classification algorithm that is then used to classify a patient as having favorable or poor prognosis. Alternatively, a given expression profile (from the subject) is evaluated by clustering or otherwise assigning the gene expression profile to an existing group with a favorable prognosis or an existing group with an unfavorable or poor prognosis. In the present invention, an elevated level of ENO1, FABP5, TRIP13, TAGLN2, or RFC4, relative to a suitable control, is associated with a poor prognosis for a subject, and, therefore, in particular embodiments, an abnormal gene expression profile comprises elevated levels of 1, 2, 3, 4, or all 5 of ENO1, FABP5, TRIP13, TAGLN2, and RFC4, relative to a suitable control. For example, in particular embodiments, the presence of an abnormal gene expression profile is determined by calculating the mean of log-normalized (e.g., $\log_2$) gene expression levels of ENO1, FABP5, TRIP13, TAGLN2, and RFC4, wherein a mean above a predetermined threshold (e.g., at least or about 10.68) indicates a poor prognosis.

"Testing" a gene expression level entails contacting a biological sample with one or more isolated reagents for detecting a gene expression level—i.e., the gene expression levels of ENO1, FABP5, TRIP13, TAGLN2, and RFC4—to measure the amount of a gene expression product by an analytical laboratory method. Testing a level of a gene expression product may be done directly in the course of the analytical laboratory method or, in some embodiments, by evaluating the quantitative output of the analytical laboratory methods.

"Isolated reagents for detecting a gene expression level" are isolated analytical reagents in substantially purified form adapted for use in detecting gene expression levels of a target analyte and include, for example, isolated oligonucleotides complementary to a nucleic acid target analyte or, in some embodiments, antibodies that specifically bind a protein target analyte. In some embodiments, isolated reagents for detecting a gene expression level are products of man that are markedly different from compounds that exist in nature. In particular embodiments, the isolated reagents for detecting a gene expression level are artificially and detectably labeled. In some embodiments, the biological sample is transformed into something markedly different in order to detect gene expression levels—i.e., the biological sample is artificially and detectably labeled, either directly, or, in some embodiments, by complexing the biological sample with isolated reagents for detecting a gene expression level that are, e.g., artificially and detectably labeled.

"Target analyte" is all or part of a gene expression product, either protein or nucleic acid, that is sufficient to identify the analyte from other compounds that might be present in a sample and, as used in this application, comprises all or part of a gene expression product for ENO1, FABP5, TRIP13, TAGLN2, or RFC4.

"Target template" refers to a nucleic acid target analyte.

Any biological sample containing cells from the subject can be used in the methods provided by the invention. In certain embodiments, the biological sample comprises fewer than about 50,000 cells, e.g., fewer than 45,000; 40,000; 30,000; 20,000; 10,000; 9,000; 8,000; 7,000; 6,000; 5,000; 4,000; 3,000; 2,000; 1,000; 900; 800; 700; 600; 500; 400; 300; 200; 100; 90; 80; 70; 60; 50; 40; 30; 20; 10; 9; 8; 7; 6; 5; 4; 3; or 2 myeloma cells. In particular embodiments, the myeloma cells are selected (e.g., by flow cytometry or laser capture microscopy) by $CD138^+$ expression, $CD38^+/CD45^{dim}$ expression, or $CD38/CD45^{neg}$ expression.

Detection Methods and Kits

To obtain a gene expression profile, two or more gene expression levels are determined. Expression levels can be determined by measuring and/or testing at the nucleic acid or protein level, or a combination thereof, as well as, in some embodiments, analyzing previously-determined levels. Any means of determining gene expression levels can be employed when practicing the methods provided by the invention. In particular embodiments, the sensitivity of the method used is such that the gene expression levels can be detected in a sample containing fewer than about 50,000 myeloma cells.

For example, levels of nucleic acid gene expression products can be determined in a number of ways, including polymerase chain reaction (PCR), including reverse transcriptase (rt) PCR, droplet digital PCR, real-time and quantitative PCR methods (including, e.g., TAQMAN®, molecular beacon, LIGHTUP™, SCORPION™, SIMPLEPROBES®; see, e.g., U.S. Pat. Nos. 5,538,848; 5,925,517; 6,174,670; 6,329,144; 6,326,145 and 6,635,427); Northern blotting; Southern blotting of reverse transcription products and derivatives; array based methods, including blotted arrays or in situ-synthesized arrays; and sequencing, e.g., sequencing by synthesis, pyrosequencing, dideoxy sequencing, or sequencing by ligation, or any other methods known in the art, such as discussed in Shendure et al., *Nat. Rev. Genet.* 5:335-44 (2004) or Nowrousian, *Euk. Cell* 9(9):1300-1310 (2010), including such specific platforms as HELICOS®, ROCHE® 454, ILLUMINA®/SOLEXA®, ABI SOLiD®, and POLONATOR® sequencing. In particular embodiments, the levels of nucleic acid gene expression products are measured by qRT-PCR. In still more particular embodiments, the qRT-PCR uses three nucleic acid sets for each gene, where the three nucleic acids comprise a primer pair together with a probe that binds between the regions of a target nucleic acid where the primers bind—known commercially as a TAQMAN® assay. In particular embodiments, primers for use in the methods provided by the invention include Hs00361415_m1, Hs02339439_g1, Hs00188500_m1, Hs00761239_s1, and Hs00427469_m1, as well as those provided in Table B and probes substantially similar to those in Table B. For example, in some embodiments, the pairs labeled "primer" for a particular gene in Table B are used. In more particular embodiments, the accompanying "probe" for the particular gene in Table B is used as well, and, in more particular embodiments, the probe includes a detectable label, such as a fluorescent label. "Substantially similar" probes can functionally substitute for those in Table B in the methods provided by the invention. In some embodiments, substantially similar sequences are 60, 65, 70, 75, 80, 85, 90, 95, 96, 97, 98, 99, 99.5, or 100% identical to the sequences in Table B; or, alternatively or additionally, substantially similar sequences have endpoints within 100, 90, 80, 70, 60, 50, 40, 35, 30, 25, 20, 19, 18, 17, 16, 15, 14, 13, 12, 11, 10, 9, 8, 7, 6, 5, 4, 3, 2, 1, or 0 nucleotides upstream or downstream of either of the endpoints of the those in Table B.

Table A—or similar nucleic acid sequences—can be of any length sufficient to distinguish the fragment from other sequences expected to be present in a mixture, e.g., at least 5, 10, 15, 20, 40, 60, 80, 100, 150, 200 or more nucleotides or at least about 5, 10, 20, 30, 40, 50, 60, 70, 80, 90, 95% of the length of the reference nucleic acid sequences in Table A.

In particular embodiments, the expression levels of one or more of the genes in Table A are measured or tested simultaneously. In some embodiments, microarrays (e.g., AFFYMETRIX®, AGILENT® and ILLUMINA®-style arrays) can be adapted for use in the methods provided by the invention. In other more particular embodiments, microarrays are not used. In other embodiments, techniques or assays with a sensitivity of only 50,000 or more myeloma cells/sample are not used.

In another related aspect, the invention provides oligonucleotide primers that are suitable for detecting (e.g., measuring and/or testing) the expression level of genes in Table A for prognosing a subject with, or suspected of having, multiple myeloma. Sets of oligonucleotide primers

TABLE B

| Gene | SequenceName | Sequence | Product |
| --- | --- | --- | --- |
| ENO1 | Probe ENO1 | AGAAGCCAAGCTCCCTGGAG | Probe |
| ENO1 | Primer ENO1 sense | GTACCGCTTCCTTAGAAC | Primer |
| ENO1 | Primer ENO1 anti-sense | CTCACATGACTCTAGACAC | Primer |
| FABP5 | Probe FABP5 | CCACTCCTGATGCTGAACCA | Probe |
| FABP5 | Primer FABP5 sense | GACTGTCTGCAACTTTAC | Primer |
| FABP5 | Primer FABP5 anti-sense | CCATCTTTCAATTTTCTTGTTA | Primer |
| TRIP13 | Probe TRIP13 | TCTTCTGGCTTCTATAACACCTGC | Probe |
| TRIP13 | Primer TRIP13 sense | GCCAGCAAGTTTTGTTTA | Primer |
| TRIP13 | Primer TRIP13 anti-sense | GCTTCTTTAGGGTGACAC | Primer |
| TAGLN | Probe TAGLN | TGATGCTGCCTCTGCCTTCT | Probe |
| TAGLN | Primer TAGLN sense | TCCTCCGTTCATTCCATG | Primer |
| TAGLN | Primer TAGLN anti-sense | GGAGAAGCATACTTGTAGAAG | Primer |
| RFC4 | Probe RFC4 | CAGCGATTACTAGACATTGCCAAGAA | Probe |
| RFC4 | Primer RFC4 sense | CAAGCCTCTGTCAGATAA | Primer |
| RFC4 | Primer RFC4 anti-sense | CCACCTGTTAATCGAGTA | Primer |

Levels of nucleic acid gene expression products can be determined by measuring and/or testing the amount of, e.g., the reference nucleic acid sequences listed in Table A, as well as complements, fragments, and similar nucleic acid sequences of the reference nucleic acid sequences listed in Table A. "Similar nucleic acid sequences" can be naturally occurring (e.g., allelic variants or homologous sequences from other species) or engineered variants relative to the reference nucleic acid sequences in Table A and will be at least about 60, 65, 70, 75, 80, 85, 90, 95, 96, 97, 98, 99% or more identical (or hybridize under highly stringent hybridization conditions to a complement of a nucleic acid sequence listed in Table A) over a length of at least about 10, 20, 40, 60, 80, 100, 150, 200 or more nucleotides or over the entire length of the reference nucleic acid sequences in Table A. Fragments of the reference nucleic acid sequences in may be prepared for any of the combinations of genes in Table A described in the application. The oligonucleotide primers provided by the invention can readily be designed using ordinary skill in the art of molecular biology to arrive at primers that are specific for a given gene in Table A (as well as fragments and similar nucleic acid sequences thereof, as described above)—i.e., so that the primers can discriminate the target nucleic acid from other nucleic acids present (or expected to be present) in a sample, including entire transcriptomes and/or primers directed to other genes in Table A. The length (e.g., about 10-100 nucleotides, e.g., about 10, 15, 16, 17, 18, 19, 20, 21, 22, 23, 24, 25, 26, 27, 28, 29, 30, 35, 40, 45, 50, 55, 60, 70, 80, 90, 100 nucleotides, or more) and sequence (i.e., the particular portion of a gene in Table A to which the primer hybridizes) of the primers can readily be adjusted to achieve a desired melting temperature ("Tm"; e.g., about 45-72° C., e.g., about 45, 50, 55, 60, 65, 70, 72° C. or more) and specificity. The skilled artisan will readily account for factors such as secondary structures, primer dimers, salt concentrations, nucleic acid concentrations, et cetera. Oligonucleotide primers provided by the invention may consist of (or consist essentially of) naturally occurring deoxribonucleotides or, optionally, may include modifications such as non-natural nucleotides, artificial backbones (such as PNAs), and detectable labels, such as florescent labels, biotinylation, et cetera.

Protein levels for genes listed in Table A, including any of the particular combinations described throughout the application, can be measured or tested by quantitative cytochemisty or histochemisty, ELISA (including direct, indirect, sandwich, competitive, multiple and portable ELISAs (see, e.g., U.S. Pat. No. 7,510,687)), western blotting (including one, two or higher dimensional blotting or other chromatographic means—optionally including peptide sequencing), RIA (radioimmunoassay), SPR (surface plasmon resonance), nucleic acid-based or protein-based aptamer techniques, HPLC (high precision liquid chromatography), peptide sequencing (such as Edman degradation sequencing or mass spectrometry (such as MS/MS), optionally coupled to HPLC), and microarray adaptations of any of the foregoing (including nucleic acid, antibody or protein-protein (i.e., non-antibody) arrays).

Protein techniques typically, but not necessarily, employ antibodies (in contrast to, for example, direct sequencing). Antibodies for use in the methods provided by the invention can be directed to a peptide sequence corresponding to any of the genes listed in Table A, as well as fragments of these sequences, similar peptide sequences, and fragments of similar peptide sequences. "Similar peptide sequences" can be naturally occurring (e.g., allelic variants or homologous sequences from other species) or engineered variants to the genes in Table A and will exhibit substantially the same biological function and/or will be at least about 60, 65, 70, 75, 80, 85, 90, 95, 96, 97, 98, 99% or more homologous (i.e., conservative substitutions (see, e.g., Heinkoff and Heinkoff, *PNAS* 89(22):10915-10919 (1992) and Styczynski et al., *Nat. Biotech.* 26(3):274-275 (BLOSUM, e.g., BLOSUM 45, 62 or 80) or Dayhoff et al., *Atlas of Protein Sequence and Structure* (Volume 5, Supplement 3), Nat. Biomed. Res. Found., pp. 345-358 (PAM, e.g., PAM 30 or 70)) or identical at the amino acid level over a length of at least about 10, 20, 40, 60, 80, 100, 150, 200 or more amino acids or over the entire length of a protein product of the genes in Table A. Fragments of protein products of the genes in Table A—or similar peptide sequences—can be of any length sufficient to distinguish the fragment from other sequences expected to be present in a mixture, e.g., at least 5, 10, 20, 40, 60, 80, 100, 150, 200 or more amino acids or at least about 5, 10, 20, 30, 40, 50, 60, 70, 80, 90, or 95% of the length of protein products of the genes in Table A.

The term "antibody," as used herein, refers to an immunoglobulin or a part thereof, and encompasses any polypeptide comprising an antigen binding site regardless of the source, species of origin, method of production, and characteristics. As a nonlimiting example, the term "antibody" includes human, orangutan, mouse, rat, goat, rabbit, sheep, and chicken antibodies. The term includes, but is not limited to, polyclonal, monoclonal, monospecific, polyspecific, humanized, fully human, camelized, single chain, chimeric, synthetic, recombinant, hybrid, mutated, and CDR-grafted antibodies. For the purposes of the present invention, it also includes, unless otherwise stated, antibody fragments such as Fab, F(ab')2, Fv, scFv, Fd, dAb, VHH (also referred to as nanobodies), and other antibody fragments that retain the antigen binding function. Antibodies also include antigen-binding molecules that are not based on immunoglobulins, as further described below.

For example, in some embodiments, the term "antibody" includes an antigen-binding molecule based on a scaffold other than an immunoglobulin. For example, non-immunoglobulin scaffolds known in the art include small modular immunopharmaceuticals (see, e.g., U.S. Patent Application Publication Nos. 2008/0181892 and 2008/0227958, published Jul. 31, 2008, and Sep. 18, 2008, respectively), tetranectins, fibronectin domains (e.g., ADNECTINS®; see U.S. Patent Application Publication No. 2007/0082365, published Apr. 12, 2007), protein A, lipocalins (see, e.g., U.S. Pat. No. 7,118,915), ankyrin repeats, and thioredoxin. Molecules based on non-immunoglobulin scaffolds are generally produced by in vitro selection of libraries by phage display (see, e.g., Hoogenboom, *Method Mol. Biol.* 178:1-37 (2002)), ribosome display (see, e.g., Hanes et al., *FEBS Lett.* 450:105-110 (1999) and He and Taussig, *J. Immunol. Methods* 297:73-82 (2005)), or other techniques known in the art (see also Binz et al., *Nat. Biotech.* 23:1257-1268 (2005); Rothe et al., *FASEB J.* 20:1599-1610 (2006); and U.S. Pat. Nos. 7,270,950; 6,518,018; and 6,281,344) to identify high-affinity binding sequences.

To perform the methods provided by the invention, the invention further provides kits comprising reagents for performing any of the methods provided by the invention. Typically, the kits provided by the invention comprise (or consist essentially of or consist of) reagents for detecting, measuring and/or testing the expression level of two or more genes in Table A, i.e., at least 2, 3, 4, or all 5 genes. The kits may include, for example, oligonucleotide primers provided by the invention, antibodies provided by the invention, or a combination thereof; in certain embodiments, these reagents are artificially and detectably labeled. Kits will typically include instructions for use. Optionally, the kits may include "suitable positive controls," which are compositions comprising (or consisting essentially of or consisting of) nucleic acids, proteins, or nucleic acids and proteins that exhibit an abnormal expression pattern of genes from Table A. For example, suitable controls may be from a clinical source known to have favorable or unfavorable multiple myeloma prognosis and may include either fixed or preserved but otherwise unprocessed biopsy tissue, or, alternatively, isolated fractions from such biopsies, including fractions comprising (consisting of or consisting essentially of) nucleic acids (e.g., mRNA or cDNAs thereof), protein, and combinations thereof (e.g., at least 20, 40, 50, 60, 70, 80, 90, 95, 97, 99% by dry weight, or more, nucleic acid and/or protein). Alternatively, in certain embodiments, the suitable positive controls may comprise artificial mixtures of nucleic acids and/or proteins, e.g., combined in proportions characteristic of an abnormal expression pattern of 2 or more genes from Table A.

Analysis

Gene expression levels can be analyzed by any means in the art. Before further analysis, raw gene expression data can be transformed, e.g., log-normalized, expressed as an expression ratio, percentile-ranked, or quantile-scaled, etc. Data may further be modified by any nonparametric data scaling approach.

Expression patterns can be evaluated and classified by a variety of means, such as general linear model (GLM), ANOVA, regression (including logistic regression), support vector machines (SVM), linear discriminant analysis (LDA), principal component analysis (PCA), k-nearest neighbor (kNN), neural network (NN), nearest mean/centroid (NM), and baysian covariate predictor (BCP). A model, such as SVM, can be developed using any of the subsets and combinations of genes described herein based on the teachings of the invention. In more particular embodiments, an expression pattern is evaluated as the mean of log-normalized expression levels of the genes.

A selected threshold for an expression profile (summarized as a risk score) can be set to achieve a desired sensitivity or specificity, and/or to stratify subjects based on a relative hazard ratio between stratification groups. For example, in some embodiments, a disease index threshold is set to achieve a "hazard ratio" (ratio of overall survival, event-free survival, or progression free survival for multiple myeloma subjects between two stratification groups, e.g., high and low risk prognosis groups) of about 1.5, 1.6, 1.7, 1.8, 1.9, 2.0, 2.2, 2.4, 2.6, 2.8, 3.0, 3.2, 3.4, 3.6, 3.8, 4.0, 4.2, 4.4, 4.6, 4.8, 5.0, 5.2, 5.4, 5.6, 5.8, 6.0, or more over a period of, e.g., 6, 12, 18, or 24 months, or 3, 4, 5, 6, 7, 8, 9, or 10 years. "Stratification groups" are the members of a data set satisfying one or more stratification criteria—for example, a percentile rank of disease index, such as all group members with a disease index greater than or equal to about the $60^{th}$ percentile or a mean log-normalized gene expression profile of less than about 5 or between about 5 and about 15, e.g., greater than about 5, 6, 7, 8, 9, 10, 11, 12, 13, 14, 15, or more, such as greater than about 8, 9, or 10, more particularly, greater than 10, e.g., greater than about 10.68. Stratification groups may be compared by any means by any statistic, such as mean, median, mode, and/or standard deviation of any clinical parameter, such as age, duration of disease, OS, PFS, et cetera.

Treatment Methods

In another aspect, the invention provides methods of treating multiple myeloma. For example, any of the methods provide by the invention can, in certain embodiments, further comprise the step of providing (e.g., administering, prescribing, or otherwise making available) a suitable myeloma therapy to the subject, e.g., one based on the subject's prognosis by the methods provided by the invention. In other related embodiments, the results of the prognostic methods provided by the invention provide a new indication for providing (e.g., administering, prescribing, or otherwise making available) or modifying a myeloma therapy to a subject and/or changing the surveillance schedule for a subject. For example, in some embodiments, a poor prognosis (high risk myeloma) by the methods provided by the invention may indicate the need to provide a more aggressive myeloma therapy (either by adding one or more treatments to a regimen and/or increasing the dose of one or more treatments), or, in some embodiments, a less aggressive treatment, focusing on patient comfort instead of eliminating disease, may be appropriate. In some embodiments, a favorable prognosis (low risk myeloma) can, in some embodiments, indicate that a more aggressive myeloma therapy can be avoided, withdrawn, or modified (e.g., removing one or more treatments from a regimen and/or decreasing the dose of one or more treatments), or in some embodiments, more aggressive therapy may be used to attempt to eliminate disease. In other embodiments, following prognosis by the methods provided by the invention, the surveillance schedule for a subject is changed—e.g., subjects prognosed with high risk myeloma may receive a more frequent surveillance schedule, while subjects prognosed with low risk myeloma may receive a less frequent surveillance schedule. Surveillance methods for subjects with multiple myeloma are well known in the art and include, for example, cytogenetics, PET (positron emission tomography) scans, MRI (magnetic resonance imaging), DWIP, bone marrow biopsy, serum or urine electrophoresis (including monitoring one or more of β2 microglobulin levels, M protein levels (gamma spike), and immunoglobulin levels (including whole Ig, heavy chain, light chain)), and any combination of the foregoing.

"Myeloma therapy" includes both established and experimental treatments for multiple myeloma in humans. In certain embodiments, myeloma therapy comprises treatment with a therapeutically effective amount of one or more agents selected from a proteasome inhibitor, an immunomodulatory drug, cisplatin (see, e.g., PubChem 84691, 441203), etoposide (see, e.g., PubChem 36462), cyclophosphamide (see, e.g., PubChem 2907), melphalan (see, e.g., PubChem 460612), cellular therapy with expanded NK cells, cellular therapy with T-cells, antibody therapy, dexamethasone (see, e.g., PubChem 5743), and combinations thereof (e.g., 1, 2, 3, 4, 5, 6, or more of any of the foregoing—termed "combination myeloma therapy").

Exemplary proteasome inhibitor myeloma therapies include one or more of bortezomib (see, e.g., PubChem 387447), carfilzomib (see, e.g., PubChem 11556711), disulfiram (see, e.g., PubChem 3117), epigallocatechin-3-gallate (see, e.g., PubChem 65064), salinosporamide A (see, e.g., PubChem 11347535), epoxomicin (see, e.g., PubChem 16760412), MG132 (see, e.g., PubChem 462382), ONX 0912 (see, e.g., PubChem 25067547), CEP-18770 (see, e.g., PubChem 24800541), MLN9708 (see, e.g., PubChem 49867936), and combinations thereof. In more particular embodiments, bortezomib and/or barfilzomib are proteasome inhibitors for use in a myeloma therapy.

Exemplary immunemodulary myeloma therapies include, e.g., thalidomide (see, e.g., PubChem 5426; in particular embodiments, an S-racemate may be used), lenalidomide (see, e.g., PubChem 216326), pomalidomide (see, e.g., PubChem 134780), apremilast (see, e.g., PubChem 11561674), and combinations thereof.

Antibody myeloma therapies include antibodies (as defined above), including, in some embodiments, neutralizing antibodies or antibodies with ADCC activity, that specifically bind to CD20 (human GeneID No. 931), SLAMF7 (SLAM family member 7, human GeneID No. 57823 (other aliases: CD319, CS1)), CD38 (human GeneID No. 952), or CD138 (human GeneID No. 6382), and as well as combinations of these antibodies.

Particular exemplary combination myeloma therapies include the treatment regimes termed total therapy (TT)2, TT3a, TT3b, TT4, TT5, or TT6. Other exemplary combination myeloma therapies include thalidomide with dexamethasone, optionally further including melphalan.

EXEMPLIFICATION

Introduction

The prognostic value of gene expression profiling (GEP) in multiple myeloma (MM) has been reported by several groups. The GEP70 model (*Blood* 109(6):2276-2284 (2007)) was developed in Total Therapy 2 (TT2), and its discriminatory power for progression-free survival (PFS) and overall survival (OS) has been validated in several published datasets in the transplant, non-transplant and relapse settings. See *Journal of Clinical Oncology* 26(29): 4798-4805 (2008); *Blood* 115(21):4168-4173 (2010); *Blood* 109(8):3177-3188 (2007); *Blood* 111(2):968-969 (2008); and *Leukemia* 22(2):459-461 (2008). We applied the GEP70 model to Total Therapy 6 (TT6), a tandem transplant trial for previously treated MM not qualifying for front-line protocols (TT3, TT4 or TT5). The 24-mo estimates of OS were 95% and 18% for low-risk and high-risk MM, respectively.

Methods

Patients

Our training data consist of 56 MM patients on TT6 and 275 on TT3a with both survival and GEP data available. An additional 166 patients on TT3b and 351 patients on TT2 were used for validation. The details of the TT2 and TT3 have been previously published elsewhere. See *Blood* 115 (21):4168-4173 (2010); *The New England Journal of Medicine* 354(10):1021-1030 (2006); *Journal of Clinical Oncology* 28(7):1209-1214 (2010); and *Blood* 116(8):1220-1227 (2010). Details of TT6 are reported in Supplemental Methods, below.

Gene Expression Profiling

GEP sample procurement and processing as well as calculations of the GEP70 risk score have been reported previously. See *Blood* 109(6):2276-2284 (2007).

Survival Estimation

PFS and OS durations were measured from start of protocol therapy; progressions included relapse or death from any cause in the former and death from any cause in the latter. OS and PFS curves were estimated with the Kaplan-Meier method (*Journal of the American Statistical Association* (53):457-481 (1958)) and compared by the log-rank test (*Journal of the Royal Statistical Society* 135(2):185-207 (172)). Hazard ratios were estimated with Cox regression models (*Journal of the Royal Statistical Society* Series B(34):187-220 (1972)) and stepwise Cox regression analysis was conducted to select an optimal multivariate model as well as provide evidence for independent prognostic power of a risk score.

Results and Discussion

We ranked all 70 probe sets included in the GEP70 risk model by their p values, based on univariate Cox regression analysis for OS in TT6 (Table 2). The top n probe sets with the smallest p values were combined to create a continuous score using similar methodology as in the GEP70 model development.

Figure 1B:
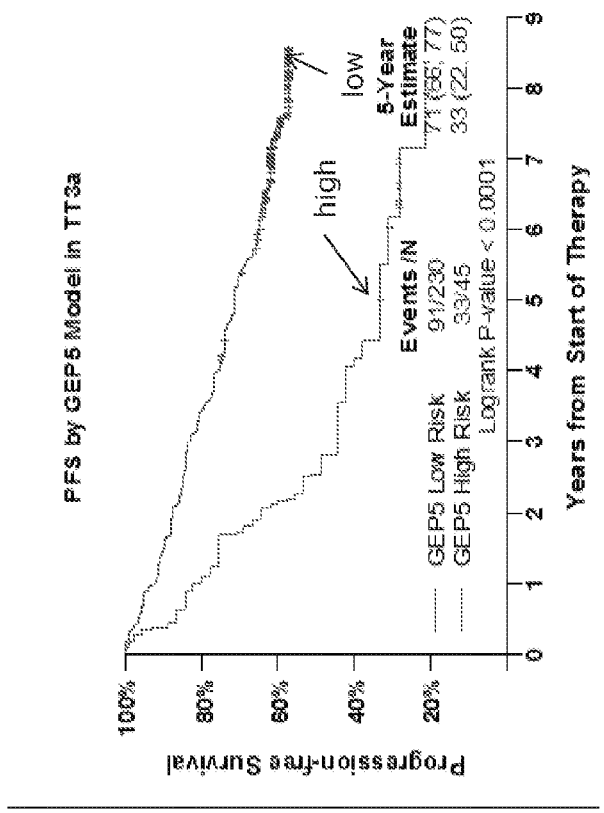
Figure 1B:
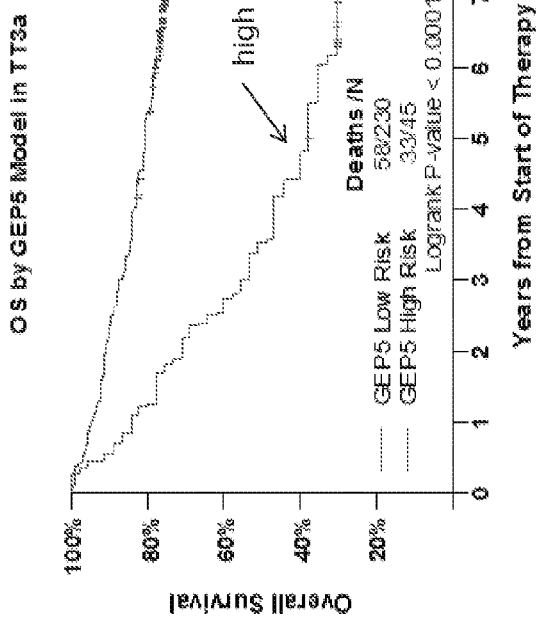
Figure 1C:
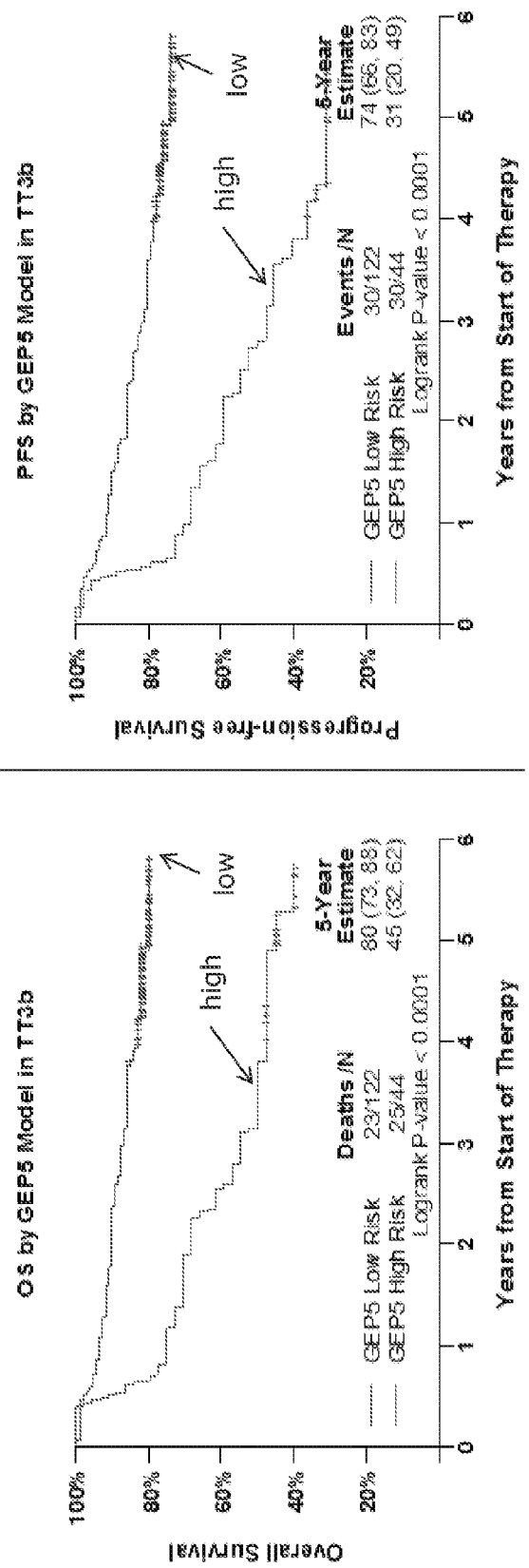
Figure 1D:
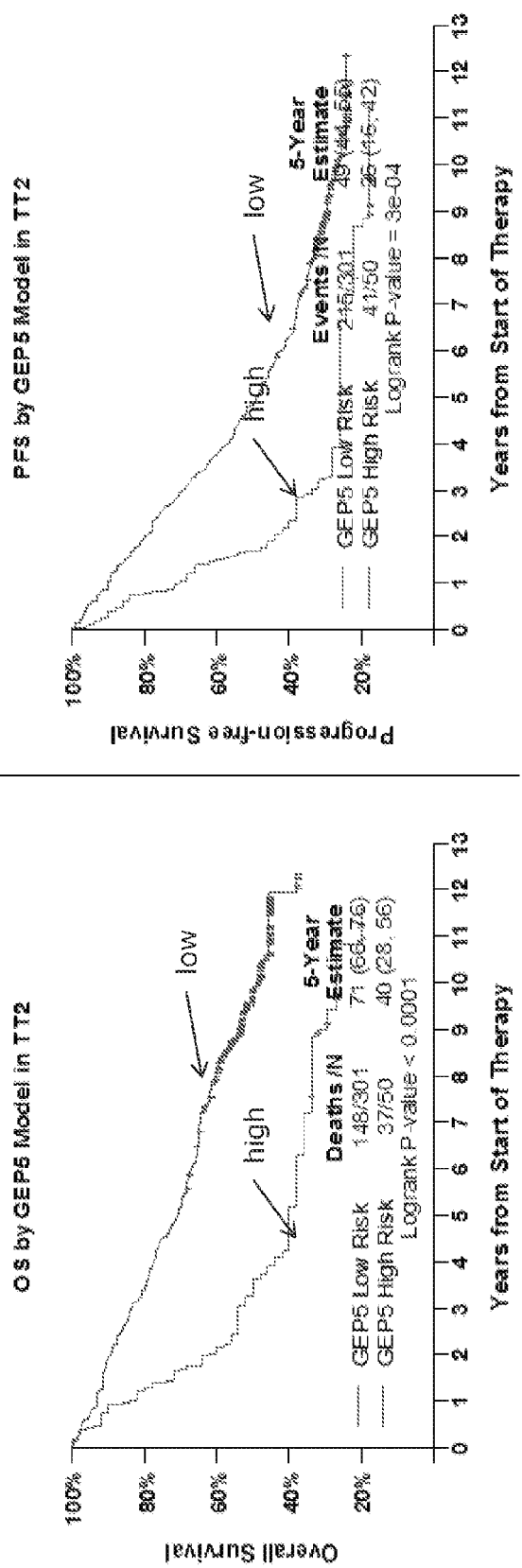
Figure 2A:
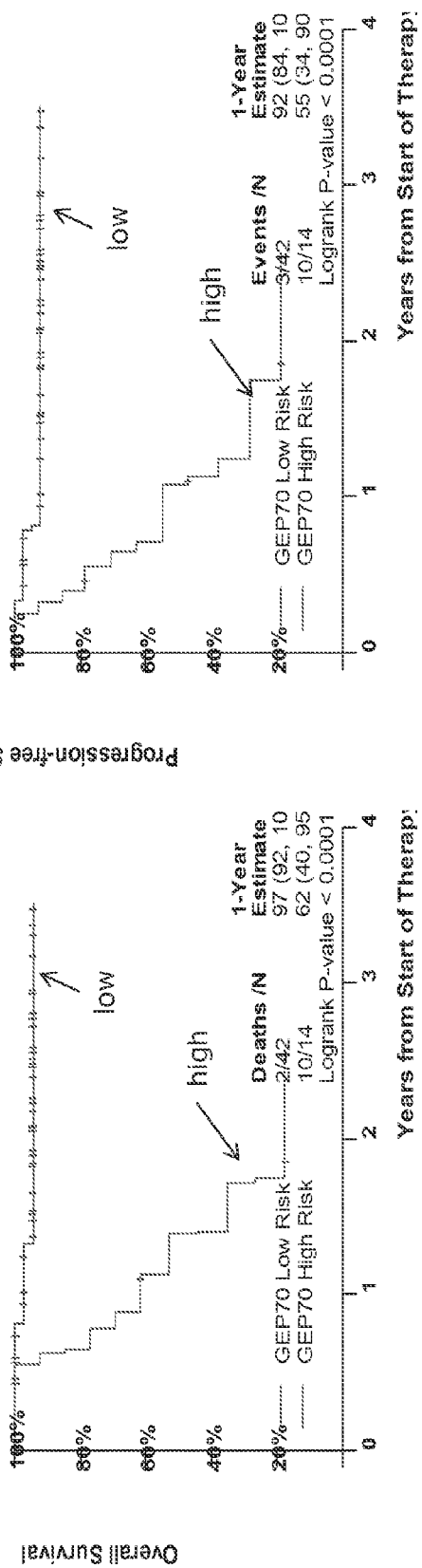
FIGS. 2A-2D are Kaplan-Meier plots illustrating that GEP70 distinguished a high- and a low-risk group with significantly different overall and progression free survival in the TT6 and TT3A training sets as well as the TT3B and TT2 validation sets using the published cut-off of 0.66.
Figure 2B:
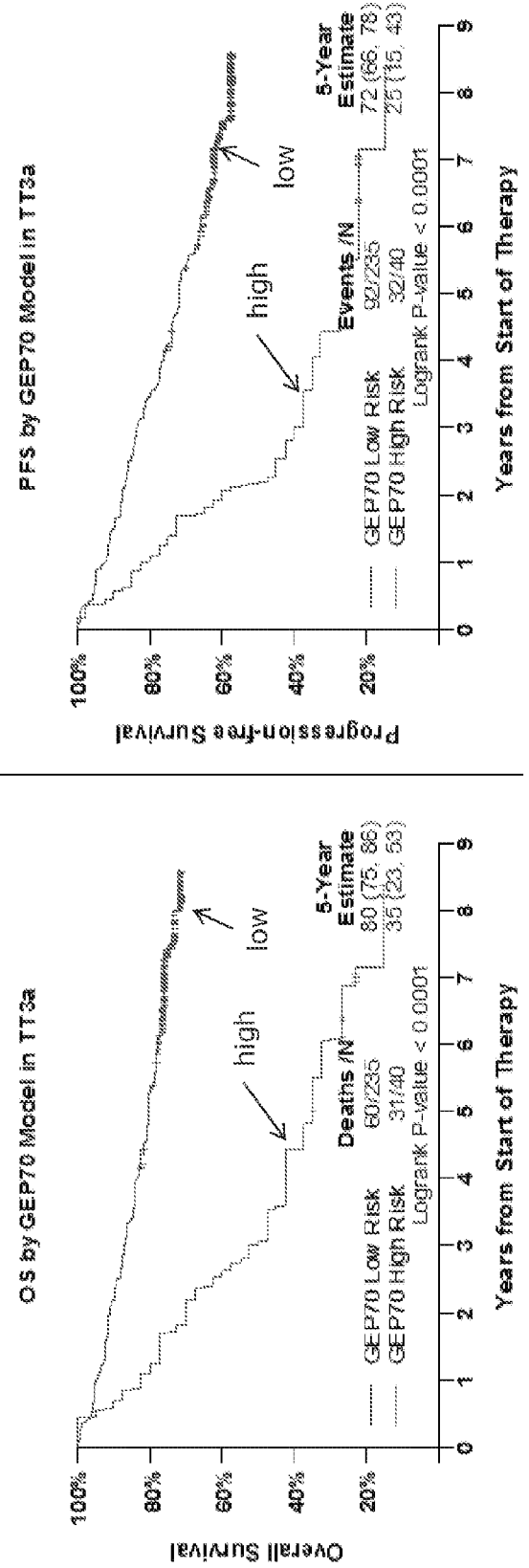
Figure 2C:
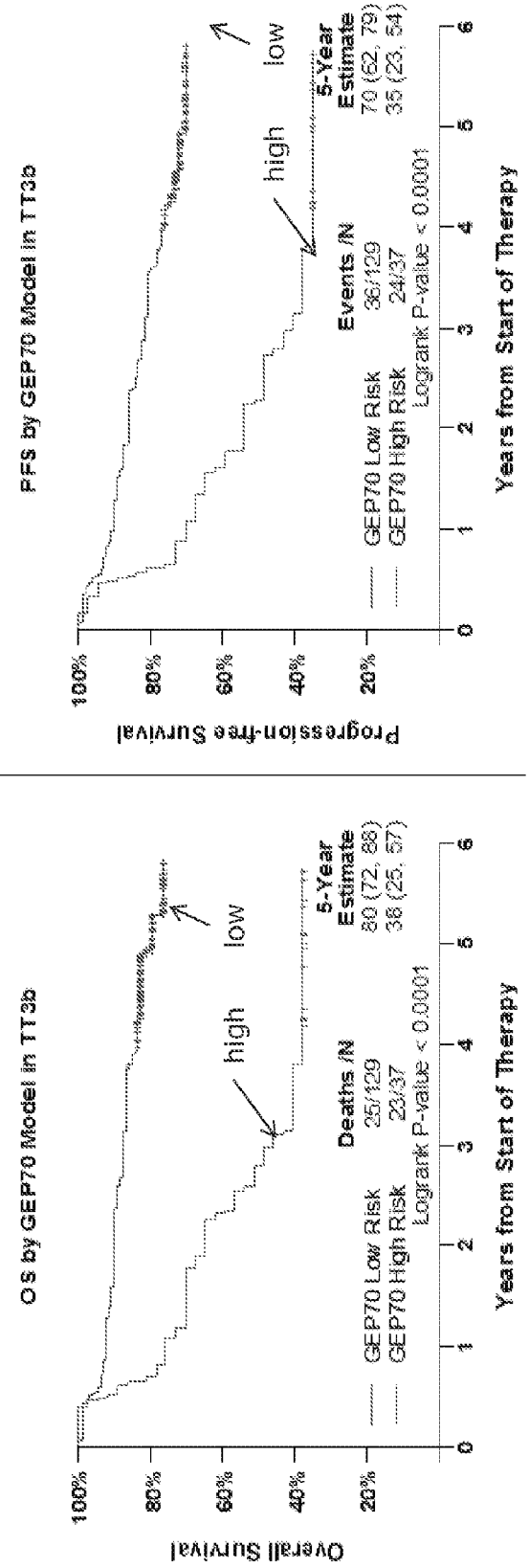
Figure 2D:
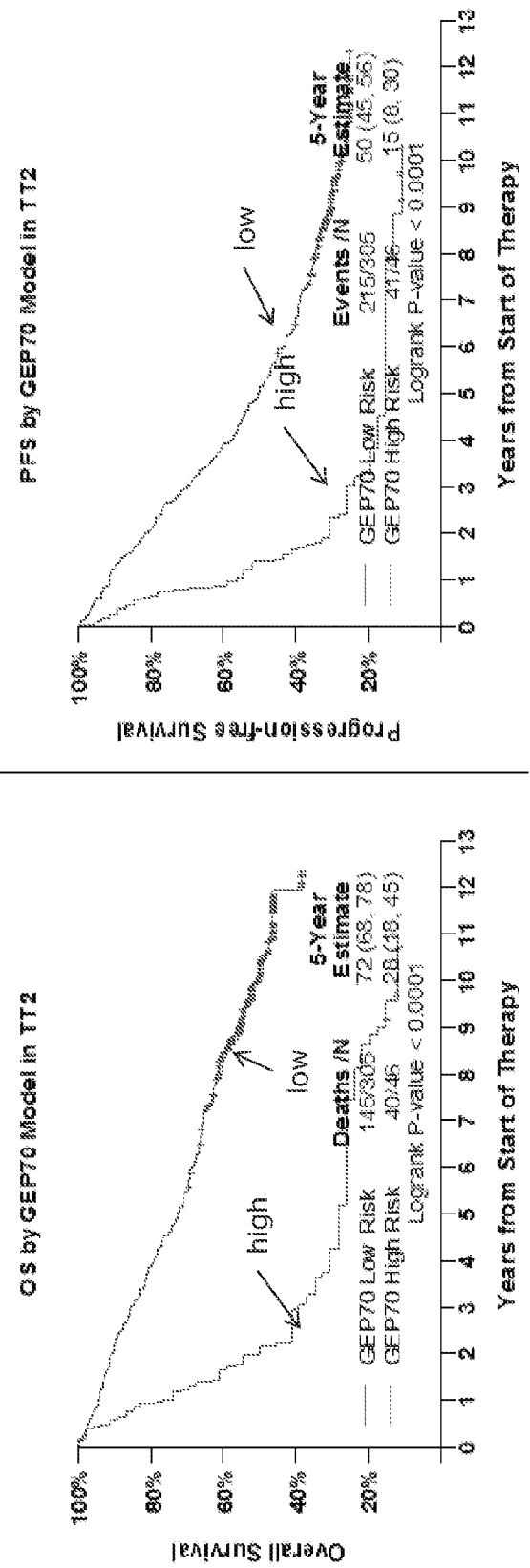
Figure 3:
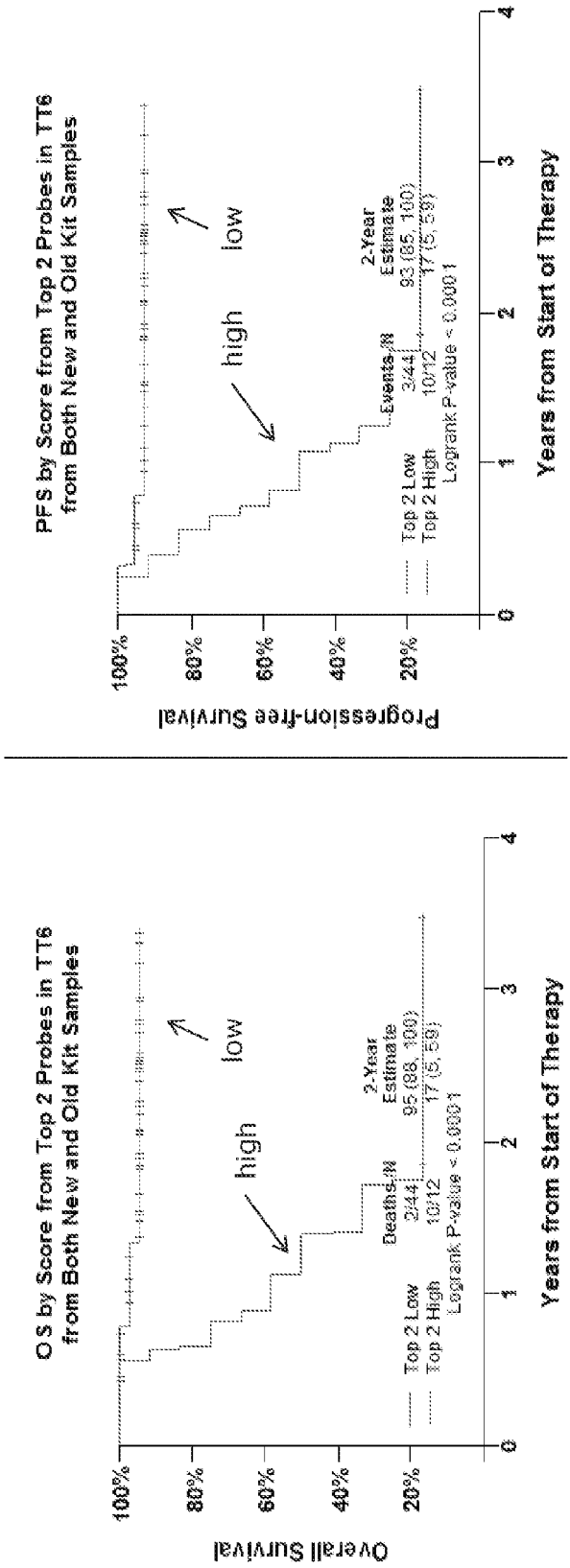
FIG. 3 provides Kaplan-Meier plots illustrating that a score from as few as 2 probes (top 2 probes in TT6 training set) differentiated between high-risk and low-risk myeloma in TT6. OS—left panel; PFS—right panel.
Figures 1, 4A:
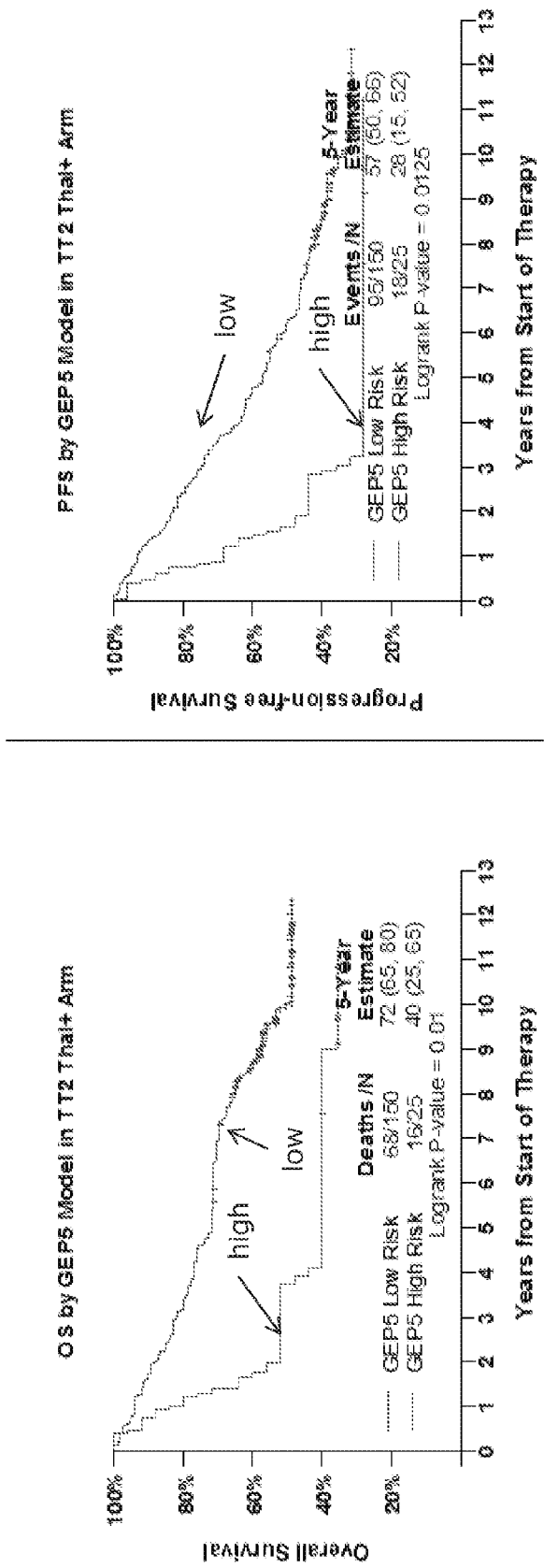
Figures 2, 4A:
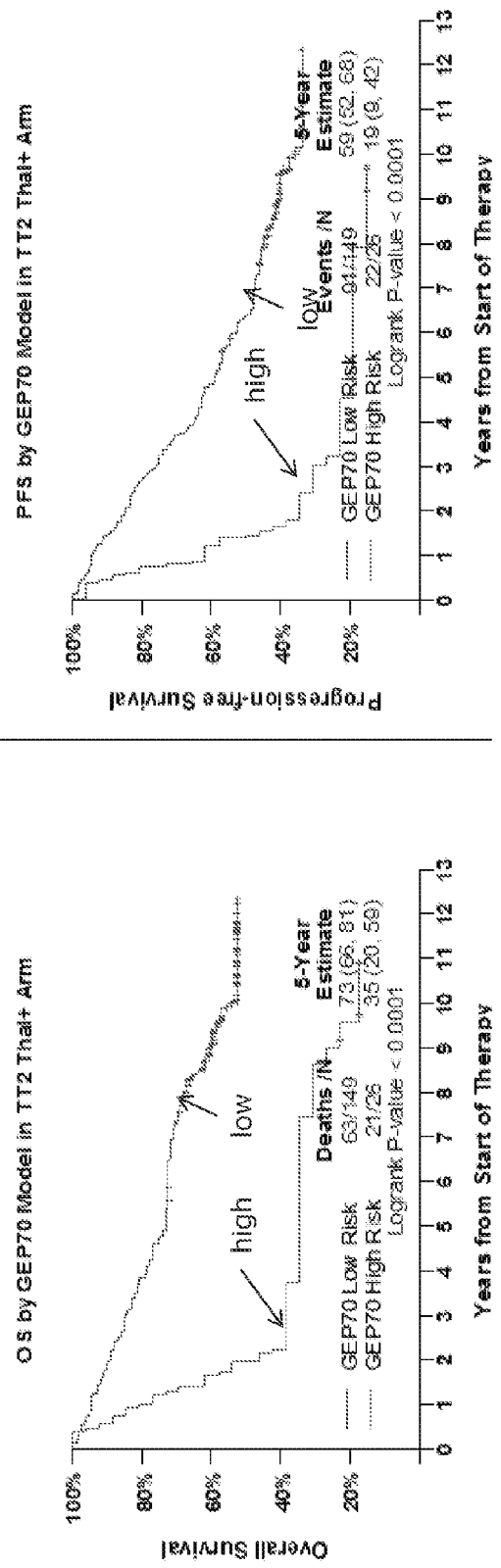
Figures 1, 4B:
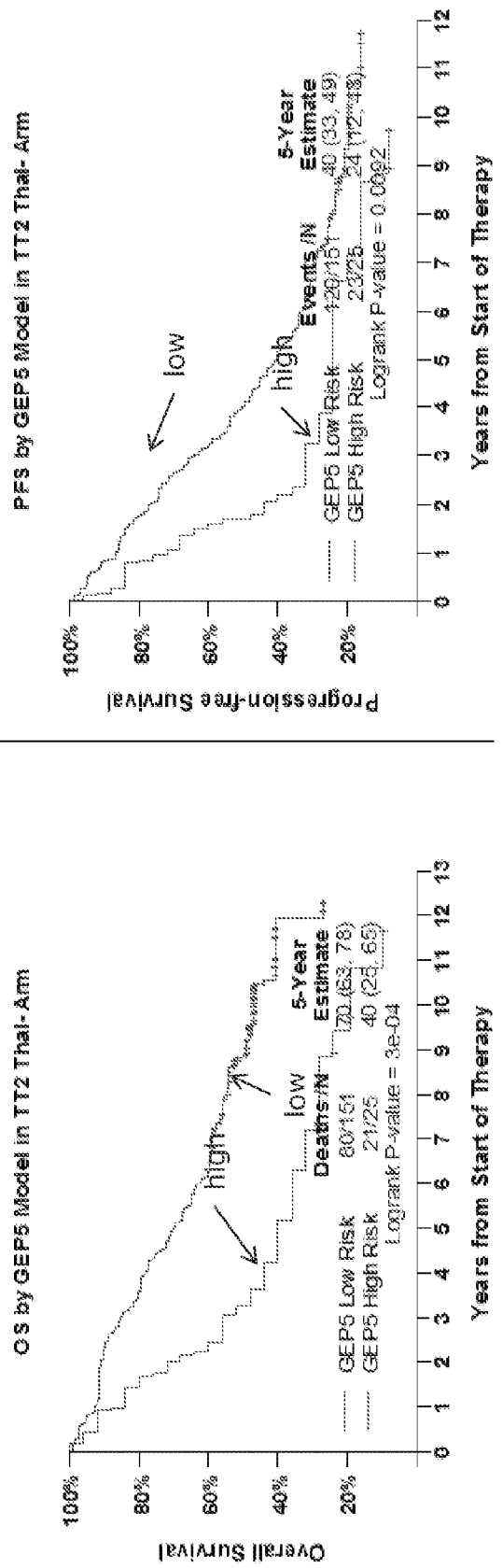
Figures 2, 4B:
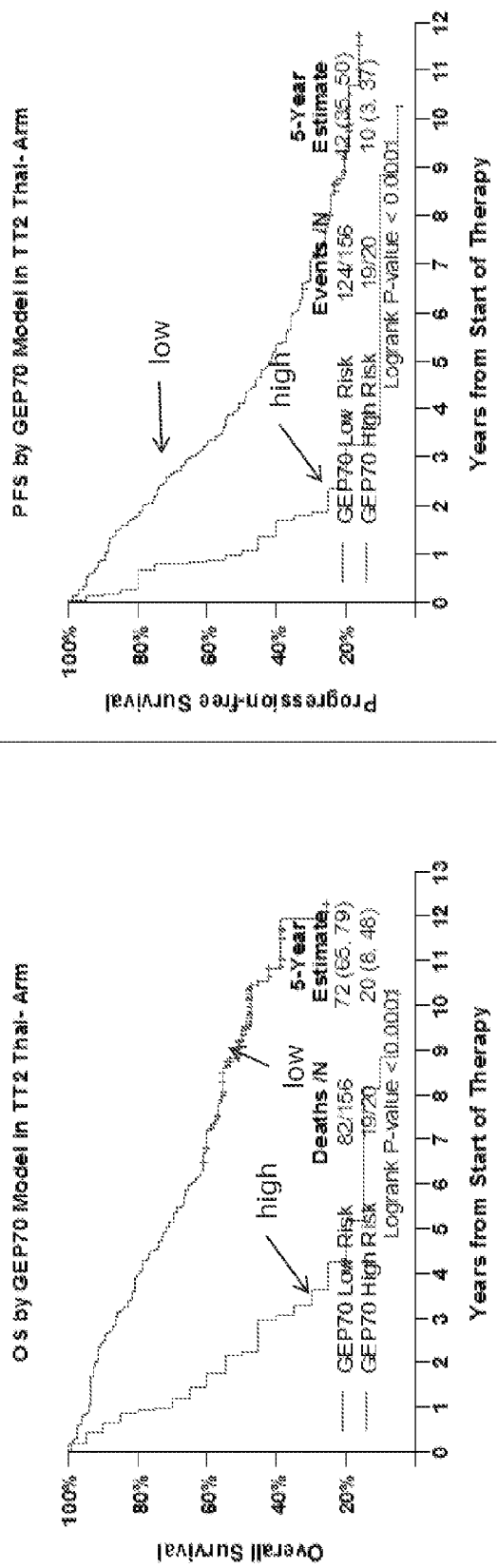

To identify a high-risk patient group, we employed the running log rank test to determine an optimal cutoff for the new risk score so that patients with scores higher than the cutoff were deemed high-risk and otherwise low-risk. We found that a model based on as few as two genes reliably predicted risk for patients with MM on TT6 (FIG. 3). Next, we selected the top five probe sets (corresponding to the genes ENO1, FABP5, TRIP13, TAGLN2, and RFC4) to form a 5-probe score (referred to as GEP5 hereafter; FIG. 1A). Since each of the five probe sets had a positive association with death rate in TT6, the GEP5 score was simply the mean of log 2 transformed expression levels of the five probe sets. Since the number of patients treated on TT6 was relatively small with a relatively short follow up, we next sought to establish the GEP5 model in a larger dataset of uniformly treated patients with a longer follow up data. Furthermore, we wanted to see whether the GEP5 was also applicable to previously untreated patients. We therefore established an optimal cutoff by the running log rank test for the GEP5 score in TT3a. In TT3a, the GEP5 score shows significant differences between high- and low-risk disease for OS and PFS which are comparable to those obtained by the GEP70 risk model using its established cutoff of 0.66 (FIG. 1B and FIG. 2B). We validated the new cutoff in TT3b, where we also observed a striking similarity between the results obtained using GEP5 and GEP70 (FIG. 1C and FIG. 2C). On multivariate analysis, the GEP5-defined high risk was selected as an independent adverse variable linked to inferior PFS with an estimated hazard ratio of 3.29 (95% CI: 1.92-5.64) but was not selected as significant for OS. The GEP70 model, in contrast, was selected for OS but not PFS (Table 3). In TT2, where the GEP70 model was developed, the GEP5- and GEP70-defined low risk groups again demonstrated highly similar clinical outcomes, although the high-risk group defined by the GEP5 model appears to have higher survival estimates than by the GEP70 model (5 year estimated OS 40% vs. 28%, 5-year estimated PFS 26% vs 15%) (FIG. 1D). This is also seen when the TT2 data are separated by treatment arm (FIG. 4). Table 1 gives a summary of the univariate survival analysis on the GEP5 and GEP70 models. Cross-tabulation of GEP70 and GEP5 risk for TT2, TT3a and TT3b showed an agreement rate of 0.90, 0.89 and 0.87, respectively (Table 3).

ENO1 encodes alpha-enolase, one of three enolase isoenzymes found in mammals. Alternative splicing of this gene results in a shorter isoform that produces a protein, MYC Binding Protein 1, which acts as a transcriptional repressor and possibly as a tumor suppressor. ENO1 is induced in diffuse large cell lymphoma (DLCL) after treatment with the natural biological agent Bryostatin1 and is up-regulated in response to enterovirus-71 (EV71) infection (at protein level). FABP5 is a member of the fatty acid binding proteins family. Over-expression of FABP5 has been associated with poor survival in triple negative breast cancer and with resistance to ATRA in a preclinical model of pancreatic ductal adenocarcinoma. TRIP13 encodes a protein that interacts with the ligand binding domain of thyroid hormone receptors, also known as hormone-dependent transcription factors. It has been suggested to play a role in early-stage non-small cell lung cancer. TAGLN has been reported as a tumor suppressor and under-expression was associated with poor prognosis in colorectal and prostate cancer, whereas it was found to be over-expressed in senescent human fibroblasts. RFC4 encodes the 37 kD subunit of the replication factor C (RFC) protein complex. RFC and the proliferating cell nuclear antigen (PCNA) are required for DNA elongation and thus proliferation of cells.

Recently, a large-scale proteomics experiment involving 85 patients with myeloma identified ENO1, FABP5 and TAGLN among a set of 24 proteins that are associated with short OS. This set of 85 patients included 47 patients who were treated on TT3b. This correlation between mRNA and protein expression supports the biologic relevance of the GEP5 model.

Supplemental Methods

Total Therapy 6 is designed as an open-label phase 2 protocol for patients with symptomatic multiple myeloma (MM) with at least one prior line of chemotherapy. Patients are treated as follows:

1) INDUCTION: MEL-10 (10 mg/m$^2$) VTD-PACE and peripheral blood stem cell collection
2) $1^{st}$ TRANSPLANT: MEL-80 (20 mg/m$^2$/day×4 days)+ VRD-PACE
3) INTERIM THERAPY: MEL-20 (5 mg/m$^2$/day×4 days)+ VTD-PACE (75%) 2 cycles
4) $2^{nd}$ TRANSPLANT: MEL-80 (20 mg/m$^2$/day×4 days)+ VRD-PACE
5) MAINTENANCE: VRD alternating with: VMD
6) Q 1 month in Year 1
7) Q 2 months in Years 2 and 3.

MEL: melphalan; VTD-PACE: bortezomib (Velcade), thalidomide, dexamethasone, cisplatin, doxorubicin, cyclophosphamide, etoposide; VRD-PACE: bortezomib (Velcade), lenalidomide (Revlimid), dexamethasone, cisplatin, doxorubicin, cyclophosphamide, etoposide; VRD: bortezomib (Velcade), lenalidomide (Revlimid), dexamethasone; VMD: bortezomib (Velcade), melphalan, dexamethasone. This protocol was approved by an Institutional Review Board.

TABLE 1

Summary of the GEP70 and GEP5 models by univariate P values when considered as binary as well as continuous variables

| Protocol | Outcome Variable | Gene Predictor | P in continuous Cox analysis | P in binary Logrank analysis |
|---|---|---|---|---|
| TT2 | OS | GEP5 | 4.23E−08 | 7.05E−05 |
|  |  | GEP70 | 1.99E−14 | 2.85E−10 |

TABLE 1-continued

Summary of the GEP70 and GEP5 models by univariate P values when considered as binary as well as continuous variables

| Protocol | Outcome Variable | Gene Predictor | P in continuous Cox analysis | P in binary Logrank analysis |
|---|---|---|---|---|
|  | PFS | GEP5 | 0.000514 | 0.000783 |
|  |  | GEP70 | 8.24E−10 | 9.84E−08 |
| TT3a | OS | GEP5 | 1.76E−10 | 3.87E−05 |
|  |  | GEP70 | 1.65E−11 | 2.98E−10 |
|  | PFS | GEP5 | 1.14E−05 | 0.001044 |
|  |  | GEP70 | 7.75E−10 | 2.75E−08 |
| TT3b | OS | GEP5 | 4.17E−10 | 5.67E−06 |
|  |  | GEP70 | 2.11E−08 | 1.09E−06 |
|  | PFS | GEP5 | 1.72E−10 | 3.35E−07 |
|  |  | GEP70 | 3.50E−08 | 1.85E−05 |

TABLE 2

Hazard ratio and p value regarding OS in TT6 for the top 20 each of the 70 probe sets in GEP70 model

| Probe Set | Gene Symbol | Chromosome Location | Original HR >= 1 | HR (95% CI) | P | Q | Rank |
|---|---|---|---|---|---|---|---|
| 201231_s_at | ENO1 | chr1p36.3-p36.2 | 1 | 4.11 (2.16, 7.82) | 0.000017 | 0.000049 | 1 |
| 202345_s_at | FABP5 | chr11q12.1 /// chr13q14.3 /// chr8q21.13 | 1 | 2.74 (1.73, 4.33) | 0.000018 | 0.000049 | 2 |
| 204033_at | TRIP13 | chr5p15.33 | 1 | 5.14 (2.28, 11.56) | 0.000077 | 0.000119 | 3 |
| 200916_at | TAGLN2 | chr1q21-q25 | 1 | 2.16 (1.47, 3.18) | 0.000086 | 0.000119 | 4 |
| 204023_at | RFC4 | chr3q27 | 1 | 5.44 (2.27, 13.06) | 0.000150 | 0.000149 | 5 |
| 202729_s_at | LTBP1 | chr2p22-p21 | 0 | 0.33 (0.18, 0.59) | 0.000195 | 0.000149 | 6 |
| 200750_s_at | RAN | chr12q24.3 | 1 | 10.15 (2.98, 34.50) | 0.000207 | 0.000149 | 7 |
| 225582_at | KIAA1754 | chr10q25.1 | 0 | 0.26 (0.13, 0.53) | 0.000217 | 0.000149 | 8 |
| 203432_at | TMPO | chr12q22 | 1 | 4.87 (2.09, 11.39) | 0.000253 | 0.000155 | 9 |
| 225834_at | MGC57827 | chr1p12 /// chr1q32.1 | 1 | 2.48 (1.51, 4.10) | 0.000371 | 0.000204 | 10 |
| 226936_at | C6orf173 | chr6q22.32 | 1 | 3.60 (1.75, 7.43) | 0.000519 | 0.000251 | 11 |
| 213628_at | MCLC | chr1p13.3 | 0 | 0.24 (0.11, 0.54) | 0.000548 | 0.000251 | 12 |
| 204092_s_at | STK6 | chr20q13.2-q13.3 | 1 | 3.64 (1.72, 7.70) | 0.000716 | 0.000295 | 13 |
| 200966_x_at | ALDOA | chr16q22-q24 | 1 | 4.15 (1.81, 9.48) | 0.000751 | 0.000295 | 14 |
| 1555864_s_at | PDHA1 | chrXp22.2-p22.1 | 1 | 16.88 (3.10, 91.81) | 0.001070 | 0.000367 | 15 |
| 227547_at | LOC388795 | — | 0 | 0.14 (0.04, 0.45) | 0.001104 | 0.000367 | 16 |
| 206364_at | KIF14 | chr1q32.1 | 1 | 2.04 (1.33, 3.14) | 0.001133 | 0.000367 | 17 |
| 210334_x_at | BIRC5 | chr17q25 | 1 | 3.33 (1.61, 6.89) | 0.001199 | 0.000367 | 18 |
| 201947_s_at | CCT2 | chr12q15 | 1 | 7.01 (2.13, 23.05) | 0.001355 | 0.000393 | 19 |
| 201897_s_at | CKS1B | chr1q21.2 | 1 | 3.69 (1.65, 8.26) | 0.001531 | 0.000421 | 20 |

In Table 2, the rows are ranked by p value from smallest to largest; false discovery rate was estimated by the Q value method. The column "Original HR>=1" indicates whether the hazard ratio of a probe set was >=1 in the original TT2 training set for GEP70 model development (1=yes; 0=no). The top five probe sets were used to generate the GEP5 model.

TABLE 3

Multivariate stepwise Cox regression analysis on TT3b test set

|  | Variable | n/N (%) | Overall Survival HR (95% CI) | P-value | Progression-free Survival HR (95% CI) | P-value |
|---|---|---|---|---|---|---|
| Multivariate | White | 148/159 (93%) | 0.42 (0.18, 1.00) | 0.049 | 0.38 (0.18, 0.82) | 0.014 |
|  | GEP70 High Risk | 36/159 (23%) | 4.43 (2.46, 8.00) | <.001 |  |  |
|  | B2M > 5.5 mg/L | 48/159 (30%) |  |  | 1.76 (1.02, 3.02) | 0.042 |
|  | GEP5 high risk | 42/159 (26%) |  |  | 3.29 (1.92, 5.64) | <.001 |
| Multivariate (without GEP70) | Female | 61/159 (38%) | 2.10 (1.16, 3.81) | 0.014 |  |  |
|  | Albumin < 3.5 g/dL | 71/159 (45%) | 2.54 (1.34, 4.81) | 0.004 |  |  |
|  | GEP5 high risk | 42/159 (26%) | 2.99 (1.63, 5.46) | <.001 | 3.29 (1.92, 5.64) | <.001 |
|  | White | 148/159 (93%) |  |  | 0.38 (0.18, 0.82) | 0.014 |
|  | B2M > 5.5 mg/L | 48/159 (30%) |  |  | 1.76 (1.02, 3.02) | 0.042 |

TABLE 3-continued

Multivariate stepwise Cox regression analysis on TT3b test set

| | Variable | n/N (%) | Overall Survival | | Progression-free Survival | |
|---|---|---|---|---|---|---|
| | | | HR (95% CI) | P-value | HR (95% CI) | P-value |
| Multivariate (without GEP5) | White | 148/159 (93%) | 0.42 (0.18, 1.00) | 0.049 | 0.37 (0.17, 0.79) | 0.010 |
| | GEP70 High Risk | 36/159 (23%) | 4.43 (2.46, 8.00) | <.001 | 3.25 (1.91, 5.54) | <.001 |

Variable considered in univariate analysis were: Age >= 65 yr, Female gender, Caucasian race, Albumin < 3.5 g/dL, B2M >= 3.5 mg/L, B2M > 5.5 mg/L, Creatinine >= 2 mg/dL, CRP >= 8 mg/L, Hb < 10 g/dL, LDH >= 190 U/L, Platelet Count < 150 x 10^9/L, Cytogenetic abnormalities, GEP70 High Risk, GEP proliferation index >= 10, GEP CD-1 subgroup, GEP CD-2 subgroup, GEP HY subgroup, GEP LB subgroup, GEP MF subgroup, GEP MS subgroup. GEP PR subgroup, TP53 deletion, GEP5 high risk
HR—Hazard Ratio, 95% CI—95% Confidence Interval, P-value from Wald Chi-Square Test in Cox Regression
NS2- Multivariate results not statistically significant at 0.05 level. All univariate p-values reported regardless of significance.
Multivariate model uses stepwise selection with entry level 0.1 and variable remains if meets the 0.05 level.
A multivariate p-value greater than 0.05 indicates variable forced into model with significant variables chosen using stepwise selection.

TABLE 4

Cross-tabulation of GEP70 and GEP5 high/low risk

| Protocol | | | GEP5 | | Agreement Rate |
|---|---|---|---|---|---|
| | | | Low Risk | High Risk | |
| TT2 | GEP70 | Low Risk | 286 | 19 | 0.90 |
| | | High Risk | 15 | 31 | |
| TT3a | GEP70 | Low Risk | 218 | 17 | 0.89 |
| | | High Risk | 12 | 28 | |
| TT3b | GEP70 | Low Risk | 115 | 14 | 0.87 |
| | | High Risk | 7 | 30 | |

It should be understood that for all numerical bounds describing some parameter in this application, such as "about," "at least," "less than," and "more than," the description also necessarily encompasses any range bounded by the recited values. Accordingly, for example, the description "at least 1, 2, 3, 4, or 5" also describes, inter alia, the ranges 1-2, 1-3, 1-4, 1-5, 2-3, 2-4, 2-5, 3-4, 3-5, and 4-5, et cetera.

For all patents, applications, and other references cited herein, such as non-patent literature and reference sequence or chemical information, it should be understood that they are incorporated by reference in their entirety for all purposes as well as for the proposition that is recited. Where any conflict exits between a document incorporated by reference and the present application, this application will control.

Headings used in this application are for convenience only and do not affect the interpretation of this application.

The described computer-readable implementations may be implemented in software, hardware, or a combination of hardware and software. Examples of hardware include computing or processing systems, such as personal computers, servers, laptops, mainframes, and micro-processors. Any of the computer-readable implementations provided by the invention may, optionally, comprise a step of providing a visual output to a user, such as a visual representation on a screen or a physical printout.

Preferred features of each of the aspects provided by the invention are applicable to all of the other aspects of the invention mutatis mutandis and, without limitation, are exemplified by the dependent claims and also encompass combinations and permutations of individual features (e.g., elements, including numerical ranges and exemplary embodiments) of particular embodiments and aspects of the invention, including the working examples. For example, particular experimental parameters exemplified in the working examples can be adapted for use in the claimed invention piecemeal without departing from the invention. For example, for material that are disclosed, while specific reference of each various individual and collective combinations and permutation of these compounds may not be explicitly disclosed, each is specifically contemplated and described herein, as are methods of making and using such compounds. Thus, if a class of elements A, B, and C are disclosed as well as a class of elements D, E, and F and an example of a combination of elements A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-groups of A-E, B-F, and C-E are specifically contemplated and should be considered disclosed from disclosure of A, B, and C; D, E, and F; and the example combination A-D. This concept applies to all aspects of this application, including elements of a composition of matter and steps of method of making or using the compositions.

The forgoing aspects of the invention, as recognized by the person having ordinary skill in the art following the teachings of the specification, can be claimed in any combination or permutation to the extent that they are novel and non-obvious over the prior art. Thus, to the extent an element is described in one or more references known to the person having ordinary skill in the art, they may be excluded from the claimed invention by, inter alia, a negative proviso or disclaimer of the feature or combination of features.

While this invention has been particularly shown and described with references to example embodiments thereof, it will be understood by those skilled in the art that various changes in form and details may be made therein without departing from the scope of the invention encompassed by the appended claims.

What is claimed is:

1. A method of prognosing a subject suspected of having multiple myeloma, comprising:
   testing the gene expression levels of enolase 1 (ENO1), fatty acid binding protein 5 (FABP5), thyroid hormone receptor interactor 13 (TRIP13), transgelin 2 (TAGLN2), and replication factor C (activator 1) 4 (RFC4) in a biological sample isolated from the subject using a method that detects gene expression levels when the biological sample comprises about 50,000 or fewer myeloma cells; and
   quantifying the gene expression levels of each of ENO1, FABP5, TRIP13, TAGLN2, and RFC4,
   wherein an elevated mean, log-normalized gene expression level of ENO1, FABP5, TRIP13, TAGLN2, and RFC4 as compared to a suitable control for each gene is associated with a poor prognosis for the subject.

2. The method of claim 1, wherein the poor prognosis is reduced likelihood of overall survival (OS) and/or reduced likelihood of progression-free survival (PFS).

3. The method of claim 1, wherein the gene expression levels are tested at the protein level or at the nucleic acid level.

4. The method of claim 1, wherein the gene expression levels are tested at the nucleic acid level.

5. The method of claim 4, wherein the gene expression levels are tested by quantitative polymerase chain reaction (qPCR), quantitative real-time polymerase chain reaction (qRTPCR), digital droplet PCR, (ddPCR), sequencing, northern blotting, or Southern blotting.

6. The method of claim 5, wherein the gene expression levels are tested by qRTPCR.

7. The method of claim 6, wherein the gene expression levels are tested by qRTPCR comprising the use of sets of three primers for each of the genes, wherein for each set of three primers at least one of the primers is detectably labeled and is subject to polymerase-dependent hydrolysis in the presence of the target template of the set of three primers.

8. The method of claim 7, wherein the at least one of the primers is detectably labeled with a fluorescent label.

9. The method of claim 6, wherein the gene expression levels are tested by qRTPCR using primers or probes selected from SEQ ID NO(s): 1-15.

10. The method of claim 1, wherein the subject is undergoing myeloma therapy.

11. The method of claim 1, which is capable of prognosing OS in a subject undergoing TT2.

12. The method of claim 1, which is capable of prognosing both OS and PFS in a subject undergoing TT3a.

13. The method of claim 1, which is capable of prognosing PFS in a subject undergoing TT3b.

14. The method of claim 1, which is capable of prognosing PFS in a subject undergoing TT4 or TT5.

15. The method of claim 14, which is capable of prognosing both OS and PFS in a subject undergoing TT4 or TT5.

16. The method of claim 1, which is capable of prognosing OS in a subject undergoing TT6.

17. A method of prognosing progression free survival (PFS) in a subject with multiple myeloma undergoing Total Therapy 3b (TT3b), comprising:
   testing the gene expression levels of enolase 1 (ENO1), fatty acid binding protein 5 (FABP5), thyroid hormone receptor interactor 13 (TRIP13), transgelin 2 (TAGLN2), and replication factor C (activator 1) 4 (RFC4) in a biological sample isolated from the subject; and
   quantifying the gene expression levels of each of ENO1, FABP5, TRIP13, TAGLN2, and RFC4,
   wherein an elevated mean, log-normalized gene expression level of ENO1, FABP5, TRIP13, TAGLN2, and RFC4 is associated with a reduced likelihood of PFS for the subject.

18. A method of prognosing progression free survival (PFS) or overall survival (OS) in a subject with multiple myeloma undergoing Total Therapy 4 (TT4) or Total Therapy 5 (TT5), comprising:
   testing the gene expression levels of enolase 1 (ENO1), fatty acid binding protein 5 (FABP5), thyroid hormone receptor interactor 13 (TRIP13), transgelin 2 (TAGLN2), and replication factor C (activator 1) 4 (RFC4) in a biological sample isolated from the subject; and
   quantifying the gene expression levels of each of ENO1, FABP5, TRIP13, TAGLN2, and RFC4,
   wherein an elevated mean, log-normalized gene expression level of ENO1, FABP5, TRIP13, TAGLN2, and RFC4 as compared to a suitable control for each gene is associated with a reduced likelihood of PFS or OS for the subject.

19. The method of claim 18, wherein the method is for prognosing OS.

20. The method of claim 18, wherein the subject is a human.

21. The method of claim 18, wherein the subject exhibits an an elevated mean, log-normalized gene expression level of ENO1, FABP5, TRIP13, TAGLN2, and RFC4 and is thereby determined to have a poor prognosis and is changed to more frequent surveillance schedule.

22. The method of claim 18, wherein the subject does not exhibit an elevated mean, log-normalized gene expression level of ENO1, FABP5, TRIP13, TAGLN2, and RFC4 and is thereby determined to have a favorable prognosis.

23. The method of claim 18, wherein the subject is undergoing treatment with a proteasome inhibitor, an immunomodulatory drug, cisplatin, etoposide, cyclophosphamide, melphalan, cellular therapy with expanded NK cells, cellular therapy with T-cells, antibody therapy, dexamethasone, and combinations thereof.

24. The method of claim 18, wherein the gene expression levels are log-normalized.

25. The method of claim 18, wherein a disease index is calculated as the mean of log-normalized gene expression levels of the genes.

26. The method of claim 18, wherein the method discriminates between poor and favorable prognosis for OS or PFS with a hazard ratio of at least 1.5, 1.6, 1.7, 1.8, 1.9, 2.0, 2.2, 2.4, 2.6, 2.8, 3.0, 3.2, 3.4, 3.6, 3.8, 4.0, 4.2, 4.4, 4.6, 4.8, 5.0, 5.2, 5.4, 5.6, 5.8, or 6.0.

27. The method of claim 18, wherein the biological sample comprises fewer than 45,000; 40,000; 30,000; 20,000; 10,000; 9,000; 8,000; 7,000; 6,000; 5,000; 4,000; 3,000; 2,000; 1,000; 900; 800; 700; 600; 500; 400; 300; 200; 100; 90; 80; 70; 60; 50; 40; 30; 20; 10; 9; 8; 7; 6; 5; 4; 3; or 2 myeloma cells.

28. The method of claim 27, wherein the myeloma cells are selected by $CD138^+$ expression, $CD38^+/CD45^{dim}$ expression, or $CD38^+/CD45^{neg}$ expression.

29. A method of prognosing a subject suspected of having multiple myeloma, comprising:
testing, by qRT-PCR, the nucleic acid gene expression levels of enolase 1 (ENO1), fatty acid binding protein 5 (FABP5), thyroid hormone receptor interactor 13 (TRIP13), transgelin 2 (TAGLN2), and replication factor C (activator 1) 4 (RFC4) in a nucleic acid sample isolated from a biological sample isolated from the subject; and
calculating the mean, log-normalized gene expression level of ENO1, FABP5, TRIP13, TAGLN2, and RFC4,
wherein an elevated mean, log-normalized gene expression level of ENO1, FABP5, TRIP13, TAGLN2, and RFC4, relative to a suitable control, is associated with a poor prognosis for the subject.

30. A method of treating multiple myeloma in a subject, comprising administering a suitable therapy to the subject on the basis of a prognosis by the method of claim 1.

31. The method of claim 1, wherein the presence of an elevated mean, log-normalized gene expression level of ENO1, FABP5, TRIP13, TAGLN2, and RFC4 is determined using a non-transitory computer-readable storage medium that provides instructions that, if executed by a processor, causes the processor to perform operations comprising:
reading data representing the gene expression levels of ENO1, FABP5, TRIP13, TAGLN2, and RFC4 determined for an isolated biological sample obtained from a subject;
analyzing the data to determine the presence of an elevated mean, log-normalized gene expression level of ENO1, FABP5, TRIP13, TAGLN2, and RFC4 as compared to a suitable control for each gene; and
providing a classification of the subject on the basis of the data analysis, wherein the presence of an elevated mean, log-normalized gene expression level of ENO1, FABP5, TRIP13, TAGLN2, and RFC4 is associated with a poor prognosis for the subject.

* * * * *

SEQUENCE LISTING

<160> NUMBER OF SEQ ID NOS: 15

<210> SEQ ID NO 1
<211> LENGTH: 20
<212> TYPE: DNA
<213> ORGANISM: Artificial Sequence
<220> FEATURE:
<223> OTHER INFORMATION: Probe ENO1

<400> SEQUENCE: 1
agaagccaag ctccctggag                                              20

<210> SEQ ID NO 2
<211> LENGTH: 18
<212> TYPE: DNA
<213> ORGANISM: Artificial Sequence
<220> FEATURE:
<223> OTHER INFORMATION: Primer ENO1 sense

<400> SEQUENCE: 2
gtaccgcttc cttagaac                                                18

<210> SEQ ID NO 3
<211> LENGTH: 19
<212> TYPE: DNA
<213> ORGANISM: Artificial Sequence
<220> FEATURE:
<223> OTHER INFORMATION: Primer ENO1 anti-sense

<400> SEQUENCE: 3
ctcacatgac tctagacac                                               19

<210> SEQ ID NO 4
<211> LENGTH: 20
<212> TYPE: DNA
<213> ORGANISM: Artificial Sequence
<220> FEATURE:
<223> OTHER INFORMATION: Probe FABP5

<400> SEQUENCE: 4
ccactcctga tgctgaacca                                              20

<210> SEQ ID NO 5
<211> LENGTH: 18
<212> TYPE: DNA
<213> ORGANISM: Artificial Sequence
<220> FEATURE:
<223> OTHER INFORMATION: Primer FABP5 sense

<400> SEQUENCE: 5
gactgtctgc aactttac                                                18

<210> SEQ ID NO 6
<211> LENGTH: 22
<212> TYPE: DNA
<213> ORGANISM: Artificial Sequence
<220> FEATURE:
<223> OTHER INFORMATION: Primer FABP5 anti-sense

<400> SEQUENCE: 6
ccatctttca attttcttgt ta                                           22

<210> SEQ ID NO 7
<211> LENGTH: 24
<212> TYPE: DNA
<213> ORGANISM: Artificial Sequence

```
<220> FEATURE:
<223> OTHER INFORMATION: Probe TRIP13

<400> SEQUENCE: 7
tcttctggct tctataacac ctgc                                               24

<210> SEQ ID NO 8
<211> LENGTH: 18
<212> TYPE: DNA
<213> ORGANISM: Artificial Sequence
<220> FEATURE:
<223> OTHER INFORMATION: Primer TRIP13 sense

<400> SEQUENCE: 8
gccagcaagt tttgttta                                                      18

<210> SEQ ID NO 9
<211> LENGTH: 18
<212> TYPE: DNA
<213> ORGANISM: Artificial Sequence
<220> FEATURE:
<223> OTHER INFORMATION: Primer TRIP13 anti-sense

<400> SEQUENCE: 9
gcttctttag ggtgacac                                                      18

<210> SEQ ID NO 10
<211> LENGTH: 20
<212> TYPE: DNA
<213> ORGANISM: Artificial Sequence
<220> FEATURE:
<223> OTHER INFORMATION: Probe TAGLN

<400> SEQUENCE: 10
tgatgctgcc tctgccttct                                                    20

<210> SEQ ID NO 11
<211> LENGTH: 18
<212> TYPE: DNA
<213> ORGANISM: Artificial Sequence
<220> FEATURE:
<223> OTHER INFORMATION: Primer TAGLN sense

<400> SEQUENCE: 11
tcctccgttc attccatg                                                      18

<210> SEQ ID NO 12
<211> LENGTH: 21
<212> TYPE: DNA
<213> ORGANISM: Artificial Sequence
<220> FEATURE:
<223> OTHER INFORMATION: Primer TAGLN anti-sense

<400> SEQUENCE: 12
ggagaagcat acttgtagaa g                                                  21

<210> SEQ ID NO 13
<211> LENGTH: 26
<212> TYPE: DNA
<213> ORGANISM: Artificial Sequence
<220> FEATURE:
<223> OTHER INFORMATION: Probe RFC4

<400> SEQUENCE: 13
cagcgattac tagacattgc caagaa                                             26
```

```
<210> SEQ ID NO 14
<211> LENGTH: 18
<212> TYPE: DNA
<213> ORGANISM: Artificial Sequence
<220> FEATURE:
<223> OTHER INFORMATION: Primer RFC4 sense

<400> SEQUENCE: 14
caagcctctg tcagataa                                                18

<210> SEQ ID NO 15
<211> LENGTH: 18
<212> TYPE: DNA
<213> ORGANISM: Artificial Sequence
<220> FEATURE:
<223> OTHER INFORMATION: Primer RFC4 anti-sense

<400> SEQUENCE: 15
ccacctgtta atcgagta                                                18
```